US010434122B2

(12) United States Patent
Shapiro

(10) Patent No.: US 10,434,122 B2
(45) Date of Patent: Oct. 8, 2019

(54) CELLULAR TRANSPLANT SITE

(71) Applicant: THE GOVERNORS OF THE UNIVERSITY OF ALBERTA, Edmonton (CA)

(72) Inventor: A. M. James Shapiro, Edmonton (CA)

( * ) Notice: Subject to any disclaimer, the term of this patent is extended or adjusted under 35 U.S.C. 154(b) by 0 days.

(21) Appl. No.: 14/863,541

(22) Filed: Sep. 24, 2015

(65) Prior Publication Data

US 2016/0082158 A1  Mar. 24, 2016

Related U.S. Application Data

(60) Provisional application No. 62/054,749, filed on Sep. 24, 2014.

(51) Int. Cl.
| A61K 35/39 | (2015.01) |
| A61L 17/00 | (2006.01) |
| A61L 15/14 | (2006.01) |
| A61L 31/04 | (2006.01) |
| A61L 31/14 | (2006.01) |
| A61K 49/00 | (2006.01) |
| A61L 27/38 | (2006.01) |

(52) U.S. Cl.
CPC .......... *A61K 35/39* (2013.01); *A61K 49/0008* (2013.01); *A61L 27/3804* (2013.01); *A61L 31/04* (2013.01); *A61L 31/146* (2013.01)

(58) Field of Classification Search
None
See application file for complete search history.

(56) References Cited

U.S. PATENT DOCUMENTS

| 7,361,158 B1 * | 4/2008 | Mooney, Jr. ...... | A61M 25/0043 604/174 |
| 9,011,899 B2 * | 4/2015 | Hasilo ................. | A61L 27/3804 424/422 |
| 2014/0134416 A1 * | 5/2014 | Burdinski ............ | C08G 77/392 428/219 |

FOREIGN PATENT DOCUMENTS

WO    WO 2011/025977    *   8/2010

OTHER PUBLICATIONS

Pepper et al Transplantation 90: Suppl 1, p. 1011, Abstract 2531, 2010.*
Kawakami et al. Cell Transplant 9: 729-32, 2000.*
Kpodonu (Man Thorac Endoaortic Surg, dated Jul. 27, 2010; pp. 1-4) online version downloaded on Feb. 3, 2017 from (http://link.springer.com/chapter/10.1007/978-1-84996-296-4_3/fulltext.ht . . . )).*
Sernova Corp (Press release dated Apr. 23, 2015).*
Chandler DL (MIT News Office Jul. 16, 2013) (downloaded on Feb. 3, 2017 (http://news.mit.edu/2013/hydrophobic-and-hydrophilic-explained-0716).*
Plastic—Wikipedia, pp. 1-19, downloaded from {http://en.wikipedia.org/wiki/Plastic}.*
Pepper: Clin Dev Immunol 2013, Article ID 352315, 13 pages; Epub Sep. 9, 2013—abstract.*
Flessner et al Adv Perit Dial 26: 101-104, 2010.*
Silastic—Wikipedia, pp. 1-2, downloaded on Jan. 17, 2018 from {https://en.wikipedia.org/wiki/Silastic}.*
Silastic Definition: 1 page, downloaded on Jan. 17, 2018 {https://www.definition-of.com/silastic}.*
Seyednejad et al (Biomat 33: 4309-4318, Mar. 2012).*
Polycaprolactone—Wikipedia, downloaded from < https://en.wikipedia.org/wiki/Polycaprolactone> on Sep. 23, 2018.*
Seyednejad et al (Biomacromol 10: 3048-3054, 2009).*
Adhikari et al (J Mater Sci 21: 1081-1089, 2010).*
Birla et al (Biotechnol Lett 31: 191-201, 2009).*
Press release, pp. 1-10, Jun. 29, 2018, downloaded from https://www.folio.ca/transplant-surgeon-changed-type-1-diabetes-treatment-the-world-over/.*
Shapiro A.M. et al.; Islet Transplantation in Seven Patients with Type 1 Diabetes Mellitus Using a Glucocorticoid-free Immunosuppressive Regimen; The New England Journal of Medicine (343), 230-238; 2000.
Ryan E.A. et al.; Five-Year Follow-Up After Clinical Islet Transplantation; Diabetes (54); 2060-2069; 2005.
Ricordi C. & Strom T.B.; Clinical Islet Transplantation: Advances and Immunological Challenges; Nature Reviews. Immunology (4); 259-268; 2004.
ed. Shapiro A.M. & Shaw J.A.; Islet Transplantation and Beta Cell Replacement Therapy; Informa Healthcare, New York, London; 2009; Chapter I, 1-27; Chapter III, 57-79; Chapter IV, 81-97; Chapter XIII, 229-249.
Harlan D.M., Kenyon N.S., Korsgren O. & Roep B.O.; Current Advances and Travails in Islet Transplantation; Diabetes (58); 2175-2184; 2009.
Plesner A. & Verchere C.B.; Advances and challenges in islet transplantation: islet procurement rates and lessons learned from suboptimal islet transplantation; Journal of Transplantation, vol. 2011.
Olsson R., Maxhuni A. & Carlsson P.O.; Revasculatization of Transplanted Pancreatic Islets Following Culture with Stimulators of Angiogenesis; Transplantation (82); 340-347; 2006.
Brissova M. & Powers A.C.; Revascularization of Transplanted Islets. Can It Be Improved?; Diabetes 57; 2269-2271; 2008.
Pepper A. R. et al.; Revascularization of Transplanted Pancreatic Islets and Role of the Transplantation Site; Clinical and Development Immunology; vol. 2013.
Merani S., Toso C., Emamaullee J. & Shapiro A.M.; Optimal Implantation Site for Pancreatic Islet Transplantation; The British Journal of Surgery (95); 1449-1461; 2008.
Vériter S., Gianello P. & Dufrane D.; Bioengineered Sites for Islet Cell Transplantation; Curr Diab Rep (13); 745-755; 2013.

(Continued)

*Primary Examiner* — Gregory S Emch
*Assistant Examiner* — Aditi Dutt
(74) *Attorney, Agent, or Firm* — Bennett Jones LLP

(57) ABSTRACT

A method of preparing a transplant site for cellular transplantation in a mammal includes the steps of inserting a foreign body comprising a biomaterial into an internal tissue; and removing the foreign body after the tissue surrounding the foreign body has undergone an inflammatory response but before significant fibrous encapsulation has occurred, leaving a neovascularized lumen suitable to receive transplanted cells or islets.

13 Claims, 14 Drawing Sheets

(56) References Cited

OTHER PUBLICATIONS

Nishimura R. et al.; Assessment for Revascularization of Transplanted Pancreatic Islets at Subcutaneous Site in Mice with a Highly Sensitive Imaging System; Transplantation Proceedings (43); 3239-3240; 2011.
Saito T. et al., Reversal of Diabetes by the Creation of Neo-islet Tissues into a Subcutaneous Site Using Islet Cell Sheets.; Transplantation (92); 1231-1236; 2011.
Sakata N. et al.; Strategy for clinical setting in intramuscular and subcutaneous islet transplantation; Diabetes/Metabolism Research and Reviews (30); 1-10; 2013.
Simeonovic C.J., Dhall D.P., Wilson J.D. & Lafferty K.J.; A comparative study of transplant sites for endocrine tissue transplantation in the pig; Australian Journal of Experimental Biology and Medical Science (64 Pt1); 37-41; 1986.
Rajab A.; Islet Transplantation: Alternative Sites; Curr Diab Rep (10), 332-337; 2010.
Anderson J.M., Rodriguez A. & Chang D.T.; Foreign Body Reaction to Biomaterials; Seminars in Immunology (20); 86-100; 2008.
Kin, T. et al.; Risk factors for islet loss during culture prior to transplantation; European Society for Organ Transplantation (21); 1029-1035; 2008.
Grainger D.W.; All Charged up About Implanted Biomaterials; Nature Biotechnology (31); 507-509; 2013.
Ricordi C., Lacy P.E. & Scharp D.W.; Automated Islet Isolation From Human Pancreas; Diabetes (38 Suppl 1); 140-142; 1989.
Anderson J.M.; Biological Response to Materials; Annual Review of Materials Research (31); 81-110; 2001.
Kenneth Ward W.; A Review of the Foreign-body Response to Subcutaneously-implanted Devices: The Role of Macrophages and Cytokines in Biofouling and Fibrosis; Journal of Diabetes Science and Technology (2); 768-777; 2008.
Fujiwara N. & Kobayashi K.; Macrophages in Inflammation; Current Drug Targets Inflammation Allergy (4); 281-286; 2005.
Nyqvist D. et al.; Donor Islet Endothelial Cells in Pancreatic Islet Revascularization; Diabetes (60); 2571-2577; 2011.
Brauker, J.H. et al.; Neovascularization of synthetic membranes directed by membrane microarchitecture; Journal of Biomedical Materials Research (29); 1517-1524; 1995.
Sharkawy A.A., Klitzman B., Truskey G.A. & Reichert W.M.; Engineering the Tissue which Encapsulates Subcutaneous Implants. III. Effective Tissue Response Times; Journal of Biomedical Materials Research (40); 598-605; 1998.
Wilson C.J., Clegg R.E., Leavesley D.I. & Pearcy M.J.; Mediation of Biomaterial-Cell Interactions by Adsorbed Proteins: A Review; Tissue Engineering (11); 1-18; 2005.
Hu W.J., Eaton J.W., Ugarova T.P. & Tang L.; Molecular Basis of Biomaterial-Mediated Foreign Body Reactions; Blood (98); 1231-1238; 2001.
Broughton G. 2nd, Janis J.E. & Attinger C.E.; The Basic Science of Wound Healing; Plastic and Reconstructive Surgery (117); 12S-34S; 2006.
Kvist P.H. et al.; Biocompatibility of an Enzyme-Based, Electrochemical Glucose Sensor for Short-Term Implantation in the Subcutis; Diabetes Technology & Therapeutics (8); 546-559; 2006.
Sharkawy A.A., Klitzman B., Truskey G.A. & Reichert W.M.; Engineering the Tissue which Encapsulates Subcutaneous Implants. I. Diffusion Properties; Journal of Biomedical Materials Research (37); 401-412; 1997.
Sharkawy A.A., Klitzman B., Truskey G.A. & Reichert W.M.; Engineering the Tissue which Encapsulates Subcutaneous Implants. II. Plasma-tissue exchange properties; Journal of Biomedical Materials Research (40); 586-597; 1998.
Zhang L. et al.; Zwitterionic Hydrogels Implanted in Mice Resist the Foreign Body Rreaction; Nature Biotechnology (31); 553-556; 2013.
Zhang H.F., Maslov K., Stoica G. & Wang L.V.; Functional photoacoustic microscopy for high-resolution and noninvasive in vivo imaging; Nature Biotechnology; (24); 848-851; 2006.
Deisseroth K.; Optogenetics; Nature Methods (8); 26-29; 2011.
Olsson R., Olerud J., Pettersson U. & Carlsson P.O.; Increased Numbers of Low-Oxygenated Pancreatic Islets After Intraportal Islet Transplantation; Diabetes (60); 2350-2353; 2011.
Pileggi A., Ricordi C., Alessiani M., & Inverardi L.; Factors Influencing Islet of Langerhans Graft Function and Monitoring; Clinica Chimica Acta; International Journal of Clinical Chemistry (310); 3-16; 2001.
Juang J.H., Peng S.J., Kuo C.H. & Tang S.C.; Three-dimensional Islet Graft Histology: Panoramic Imaging of Neural Plasticity in Sympathetic Reinnervation of Transplanted Islets under the Kidney Capsule; American Journal of Physiology, Endocrinology and Metabolism (306); E559-E570; 2014.
Stendahl J.C., Kaufman D.B., & Stupp S.I.; Extracellular Matrix in Pancreatic Islets: Relevance to Scaffold Design and Transplantation; Cell Transplant (18); 1-12; 2009.

* cited by examiner

CELLULAR TRANSPLANT SITE

FIELD OF THE INVENTION

This invention relates to methods of preparing a transplant site for islet and cellular transplantation, and the use of a biomaterial in the preparation of a transplant site.

BACKGROUND

Cellular transplantation is an attractive and growing treatment strategy for a variety of diverse disease processes including diabetes, Parkinson's, myocardial ischemia, single-gene liver defects, hemophilia and hypoparathyroidism. Transplantation of human cancer cells into mice may help to direct therapies using personalized medicine approaches. The availability of genetically engineered stem cells now provides many possibilities for therapeutic cellular replacement in regenerative medicine.

Intrahepatic transplantation of isolated insulin-secreting pancreatic islets of Langerhans is a prototypic example of a highly successful cellular replacement therapy in patients with type 1 diabetes mellitus (T1DM) with unstable glucose control. The "Edmonton Protocol" became a milestone by reporting high rates of insulin independence after islet transplant in patients with difficult-to-control diabetes[1]. Long-term analysis of these initial results indicated that insulin independence was not durable. Most patients returned to moderate amounts of insulin approximately five years post-transplant, while maintaining the absence of recurrent hypoglycemia[2].

The intrahepatic vascular space provides nutritional and physical support for islets after islets are stripped of their vascularized and specialized extracellular matrix[3,4]. Transplanting islets within the liver has been associated with procedural risks of bleeding and thrombosis, and localized steatosis. Additional factors leading to gradual graft attrition suggest that the liver may not be the optimal site for cellular transplantation of insulin-secreting cells[5,6]. The death of significant numbers of intraportal islets in the immediate post-transplant period from tissue-factor triggered platelet injury (the instant blood mediated inflammatory reaction), compounded by ischemia from immature revascularization contribute to impaired islet survival and function long-term[7]. To regain proper islet function, new blood vessels need to form around and within the graft; however, these newly formed vessels result in a vascular density that is chronically lower than that within the native islets[8,9]. This is irrespective of whether the islets are transplanted into the kidney, spleen, or infused intraportally[9]. The vascular density is not influenced by hyperglycemia or engraftment time, but numerous vessels form in the surrounding connective tissue[8].

As new, alternative stem cell derived insulin-secreting cells become available, easily retrievable sites become an imperative priority as the safety profile of potentially teratogenic cell lines are defined in patients. As a consequence, intensified research effort has been dedicated to the pursuit of alternative transplant sites[9-11].

It has been suggested that an optimal cellular transplantation site should: 1) have an adequate tissue volume capacity, 2) be in close proximity to vascular networks, ensuring sufficient oxygen supply prior to revascularization, 3) allow for dynamic communication between the cellular graft and systemic circulation in a physiologically relevant manner, 4) facilitate a minimally invasive means to transplant, biopsy and retrieve if required, and 5) elicit minimal inflammation to reduce immunogenicity and promote long-term survival[11].

The subcutaneous site is an attractive surrogate for portal vein islet infusion, due to the minimally invasive and simplistic characteristics of transplanting into this space, as well as the potential to monitor the cellular transplant through novel imaging techniques[12-14]. However, transplantation of islets into an unmodified subcutaneous site has universally failed to reverse diabetes in animal models and in human studies, due to poor oxygen tension and hypovascularity[15]. Stimulation of angiogenesis is a critical determinant of successful subcutaneous cell transplant therapy[9,11,14,16]. The use of oxygen generators, macro-device polymers, meshes, encapsulation technologies, matrices and growth factors including fibroblast growth factor, hepatocyte growth factor, vascular endothelial growth factor and co-transplantation of mesenchymal stem cells have been explored with some success. Inopportunely, the foreign body and inflammatory reaction at the interface between the host tissue and implanted biomaterial persists for the in vivo lifetime of the implant[17]. Ultimately, this response forms a thick avascular collagenous fibrotic capsule, which physically separates the biomaterial from the host. This in turn hinders metabolic exchange, cell signaling, healing, tissue-device integration, and the formation of microenvironments for opportunistic bacterial infections and ultimately engraftment failure[17,18].

Few alternative islet engraftment strategies have translated into the clinical setting, and the inventor is not aware of any that have rendered patients completely independent of insulin. There remains a need in the art for methods of cellular transplantation which may improve upon the prior art.

SUMMARY OF THE INVENTION

The present invention relates to a novel transplant technique, permitting successful cellular transplantation into an internal tissue, including but not limited to the transplantation of functional islets and stem cells. The transplant site, which may be hypoxic and avascular, is transformed into a vascularized transplant site by the host's innate foreign body response. This transformation is accomplished by the temporary implantation of a foreign body comprising a biomaterial, such as a medically approved angiocatheter, to induce a foreign body response. Once inflammatory and proliferation phases subside, which may be approximately 3-6 weeks post-implant, the biomaterial is withdrawn, and the foreign body response ends. The inflammatory processes subside, but before they subside, they have facilitated formation of a vascularized collagen scaffold with the capacity to accommodate transplant cells infused into the newly vascularized space. Removal of the implant preferably occurs before significant avascular and fibrotic changes make the transplant site unsuitable. In one embodiment, this transplant technique may permit the reversal of diabetes by placing insulin-producing islets or stem cells under the skin without need for a permanent device, matrix or exogenous growth factors.

Therefore, in one aspect, the invention may comprise a method of preparing a transplant site for cellular transplantation in a mammal, comprising the steps of:

(a) inserting a foreign body comprising a biomaterial into an internal tissue; and (b) removing the foreign body after tissue surrounding the foreign body has undergone a foreign body response, leaving a neovascularized lumen suitable to receive transplanted cells, such as islets or stem cells.

In one embodiment, the foreign body is removed before fibrous encapsulation of the transplant site occurs.

The internal tissue space may comprise a subcutaneous layer, a peritoneal layer, an intramuscular layer, a submucosal layer, an intra-bone marrow space, an intra-organ layer or an organ.

Preferably, no exogenous biological factor is used together with the foreign body.

In another aspect, the invention may comprise a method of treating a disease responsive to cellular replacement therapy, comprising the method of preparing a transplant site described herein, and further comprising the further step of transplanting cells into the lumen, which cells produce a therapeutic substance. In one embodiment, the disease responsive to cellular replacement therapy comprises diabetes, ischemic injury, Parkinson's disease, congenital hepatic defect, hemophilia, or hypoparathyroidism.

In one embodiment, the method may further comprise the use of an imaging technique to track and monitor survival of the transplanted cells and immunological response. The imaging technique may comprise photoacoustic ultrasound.

In one embodiment, the transplanted cells may comprise cells with a light sensitive ion channels and which secrete a therapeutic agent, and the method may comprise the further step of shining a light of a wavelength to activate the ion channels.

In one embodiment, the transplanted cells may comprise stem cells.

In another embodiment, the invention may comprise a method of determining a tumor sensitivity to a therapeutic agent, comprising the steps of:

(a) preparing a transplant site in an animal in accordance with the methods described herein;
(b) transplanting tumor cells into the transplant site;
(c) treating the animal with a therapeutic agent; and
(d) assessing the tumor cells response to the therapeutic agent in vivo.

In another aspect, the invention may comprise an internal tissue transplant site, formed by inflammatory, proliferation and repair processes in response to the insertion of a foreign body biomaterial and subsequent removal of the biomaterial, wherein said transplant site comprises a lumen having a newly formed, neovascularized collagen scaffold.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

Figure 1:
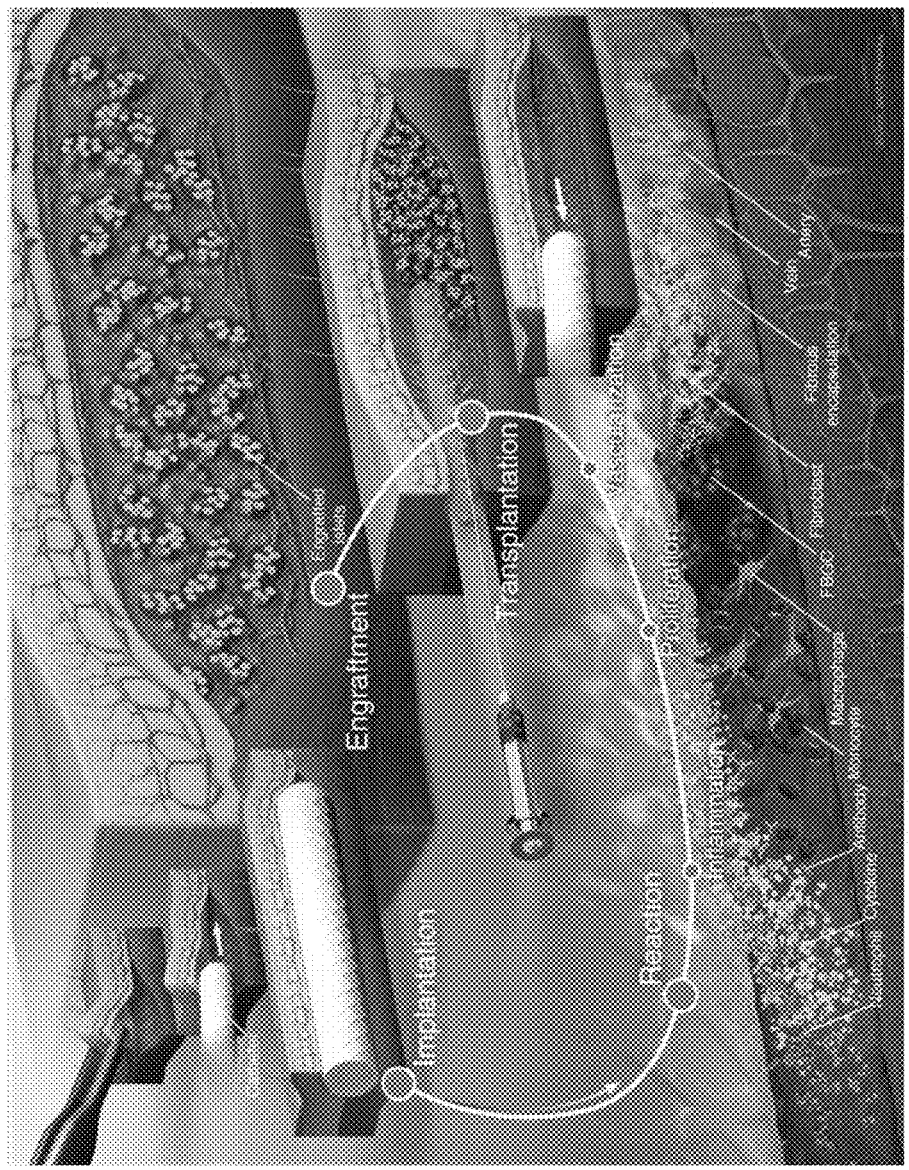
FIG. 1. A schematic representation of design and characteristics of the subcutaneous cellular transplant site.

The present invention relates to a method of preparing an internal tissue transplant site, for cellular transplantation, by harnessing the foreign body reaction to a foreign biomaterial. Unlike prior art approaches, the present invention does not use a permanent medical device to house a cellular graft, nor does it require exogenous biological agents.

As used herein, "cellular transplantation" includes the transplant of any living cells into a recipient. Without limitation, the cells may comprise stem cells or mature cells, and may be genetically modified in some cases. The transplant may be autogeneic or syngeneic, or may be a xeno-transplant or an allotransplant. The cells may be clustered or aggregated. In one embodiment, the transplanted cells may comprise pancreatic insulin-producing islet cells.

In many cases, the foreign body response or reaction is one to be avoided. Biomaterial scientists have successfully developed means to circumvent the foreign body response induced by medical devices, catheters, prosthetics, biosensors and other medical implant applications[17, 21, 22, 26, 30-32]. In contrast, the present invention harnesses the foreign body response in order to create a viable transplant site.

The foreign body response is a well-known and studied physiological process, where a subject mounts an immunologic response to substances not recognized as "self". The foreign body response is a natural and intrinsic response to a biomaterial, and can be characterized by four generalized phases: implantation, inflammation (protein adsorption), proliferation/repair (matrix deposition and neovascularization) and remodeling (fibrous encapsulation)[17, 18]. If a foreign body biomaterial implant is left in place, the foreign body response continues to remodel throughout the lifetime of the implant, eventually resulting in an avascular fibrotic granular capsule engrossing the implant[17, 18, 22, 26, 31, 32]. This chronic inflammatory response may contribute to transplant graft attrition throughout time. Therefore, by removing the foreign body at an appropriate time, the chronic stimulus may be removed. The foreign body response stimulates blood vessel growth and tissue deposition and avoids the deleterious consequences associated with chronic inflammation.

In one embodiment, the entire biological response is triggered by the implant of the foreign body, and no exogenous biological factors are used. For example, no oxygen generators, vascularization agents, growth factors, or stem cells are co-implanted or co-administered with the implant.

The foreign body reaction commences immediately upon physical contact of the biomaterial with host blood, lymph, exudate, and other endogenous fluids; resulting in the spontaneous adsorption of diverse conformations of host proteins, such as albumin, fibrinogen, complement, fibronectin and γ-globulin, on the surface of the biomaterial[17, 21, 22]. Host cells which are responsible for normal wound healing encounter this adsorbed-protein layer. Within hours of implantation, neutrophils are recruited to the inflammatory site through diapedesis and react to the unique protein layer at the biomaterial interface. Within the next several days, these cells release cytokines, chemokines, reactive oxygen species and other enzyme products that recruit tissue-resident macrophages and undifferentiated monocytes to the transplant site[17, 21, 22]. As macrophages respond to the implanted biomaterial, their phagocytic abilities are impeded by the biomaterial, resulting in their fusion into foreign-body giant cells (FBGCs). These nascent macrophages and FBGCs secrete their own milieu of signaling molecules (ie. IL-1, IL-6, IL-10, IL-12, TNF-α, TGF-β), attracting fibroblasts, which produce collagen in parallel to a period of cellular proliferation and neovascularization[17, 23]. These processes continue until a distinct, dense collagenous fibrotic capsule is created around the implant, isolating it from the host[17, 18].

As used herein, "foreign biomaterial" means a material which may safely be implanted in a mammal, and which elicits a foreign body response from the mammal. Foreign biomaterial may include, without limitation, any material such as a plastic, metal or ceramic used in medically-approved devices, and may be exemplified by existing and well-known medical devices such as catheters. In a preferred embodiment, the foreign biomaterial comprises a textured or porous surface, and more preferably, a textured and porous surface. Without restriction to a theory, it is believed that textured and porous surfaces increase the surface area of the implant, which increases the interaction with the host, and the surface area of the resulting lumen.

The surface chemical, physical and morphological characteristics of the biomaterial are known to modulate the foreign body reaction, especially in the first few weeks following the implantation of a medical device or biomaterial[17]. Hydrophobic based biomaterials have been shown to decrease macrophage adhesions and induce apoptosis[22], whereas porous and textured materials are capable of inducing the robust growth of neovascularization into the peri-implant region[22, 25, 26]. These surface properties dictate the adhesion and sustainability of immune cells on protein-engrossed surfaces[27]. It has been suggested that the degree and composition of surface adsorbed proteins mediate the subsequent inflammatory and wound healing reactions to an implanted body[27, 28]. Because a biomaterial's ability to adhere blood protein will determine its downstream ability to produce a provisional matrix, stimulate an inflammatory reaction, recruit macrophages and fibroblasts which ultimately form the transplant-supporting matrix, preferred embodiments may use biomaterials which adhere to blood proteins.

In one embodiment, the foreign biomaterial may comprise a nylon or silicon material such as that used in conventional catheters. Nylon is a generic term for a polymer comprising thermoplastic aliphatic or semi-aromatic polyamides. In one embodiment, a textured nylon catheter material has been shown to be more efficacious compared to silicone-based biomaterials with smooth composition. Without restriction to a theory, it is believed that hydrophilic materials allow blood proteins to better adhere than hydrophobic materials, and may be preferable as a result.

In one embodiment, the biomaterial is sufficiently hydrophilic to create a contact angle with water less than 90°, preferably less than 80°, and more preferably less than or equal to about 70°. Nylon 6,6 has a contact angle with water of about 68°, while nylon 7,7 has a contact angle of 70°. Very hydrophilic biomaterial surfaces may have a contact angle with water of 30° or less.

In another embodiment, the biomaterial has a critical surface tension of greater than about 20 dynes/cm, preferably greater than 30 dynes/cm, and more preferably greater than about 40 dynes/cm. Nylon 6,6 has a critical surface tension of 42.2 dynes/cm, while nylon 7,7 has a critical surface tension of about 43 dynes/cm.

As shown in Table 1 below, more hydrophobic materials, as measured by critical surface tension and by water contact angle, were not as successful in reversing diabetes in mice with syngeneic transplanted islets as the more hydrophilic nylon material.

TABLE 1

Source biomaterials for creating the subcutaneous transplant site

| Generic Name and Composition | Diameter[1] | Average Transplant Dose (islets/rec.) | Reversal of Diabetes (%) | n (recipients) | Critical Surface Tension of Biomaterial (dynes/cm) | Water Contact Angle |
|---|---|---|---|---|---|---|
| T-Tube Rubber | 8.0 fr. | 1,350 | 0 | 5 | 27* | 112.1* |
| I.V. Catheter Fluorinated Ethylene Propylene | 4.0 fr. | 500 | 50.0 | 4 | 19.1 | 108.5 |
| Long-term Indwelling Catheter Silicone | 5.0 fr. | 500 | 33.3 | 12 | 20.1** | 107.2** |
| Long-term Indwelling Catheter Silicone | 6.5 fr. | 500 | 64.7 | 17 | 20.1** | 107.2** |
| Radiopaque Angiocatheter Nylon | 5.0 fr. | 500 | 91.3 | 23 | 43.9# | 62.6# |

[1]French catheter scale;
*Butyl rubber,
**Polydimethylsiloxane,
Nylon 6 (Aramid™)

Data in Table 1 indicates that the dimensions of the implant may also be a factor influencing successful cellular transplants. The fluorinated ethylene propylene (FEP) implant demonstrated successful results despite being highly hydrophobic (water contact angle of about 108°). This may be attributed to the smaller diameter of the implant—4.0 fr., which equals 1.33 mm. As a result, although the inflammatory response to the FEP implant may not have been as robust as with the nylon implant, the resulting lumen may still be sufficiently vascularized relative to the smaller diameter of the lumen. As a result, the subsequently transplanted cells may be in sufficient proximity to the blood supply to thrive. Therefore, in one embodiment, the foreign body has a diameter of less than about 2.2 mm, preferably less than about 1.7 mm, and more preferably less than about 1.5 mm.

In one embodiment, biomaterials may be further engineered or chosen to improve the neovascularization response in the transplant site, while minimizing formation of a fibrotic capsule. For example, in an alternative embodiment, zwitterionic polymers may be used, as they have been demonstrated to hinder the foreign body response creating fibrotic capsules, while increasing the blood vessels density around an implant[18, 33].

The transplant site may comprise any internal tissue. Embodiments of the present invention are intended to create a transplant site with sufficient vascularity to allow subsequently transplanted cells to thrive. Therefore, in one embodiment, the transplant site may be ordinarily unsuitable and may be transformed into a suitable site, for example, the transplant site may be in the subcutaneous layer. In another embodiment, the transplant site may be any suitable site which is enhanced by the methods of the present invention. For example, the transplant site may be in the peritoneum, for example the omentum, a site within an internal organ, an intramuscular layer, a sub-mucosal layer, intra-bone marrow, or an intra-organ layer.

As used herein, "subcutaneous" means the tissue layer underlying the dermal layers of skin. The subcutaneous layer may also be known as the hypodermis. The subcutaneous layer is conventionally considered to be an inadequate cellular transplant site because of poor oxygenation and hypovascularization. In one embodiment, the present invention relates to the preparation of a subcutaneous transplant site, or another conventionally unsuitable site, by "prevascularization" of the site.

In one embodiment, the use of a transplant site prepared in accordance with the methods described herein may be adapted to cellular replacement therapies to treat diverse pathologies, including but not limited to, diabetes, ischemic injury, Parkinson's, congenital hepatic defect, hemophilia and hypoparathyroidism. In addition, the use of genetically engineered stem-cells for regenerative medicine requires a site for cellular engraftment and a major obstacle is the placement of these cells into a contained and potentially retrievable site. The methods described herein may provide such an environment, allowing for the safe transplantation of endocrine derived stem cells that could be retrieved should complications arise or is otherwise desired.

Post-transplant insulin independence may be notably delayed in recipients of the DL islet transplants compared to the standard renal subcapsular route. Speculation into the causation of this phenomenon has been well documented, because it manifests in the preclinical and clinical setting when islets are intraportally transplanted[36]. Acutely post-transplant islet grafts are left avascular, denervated and isolated from their endogenous cell-to-cell and extracellular matrix contacts, due to the processes involved in their isolation from the pancreas parenchyma. Islet graft revascularization is not typically observable until about 2 weeks post-transplant[37]; while intra-islet graft, perivascular sympathetic re-innervation is observed 6-weeks post-transplant to a nerve density of approximately 40% of pancreatic islets in situ[38]. These factors and the loss of islet extracellular matrix[39] have been suggested to be major causations in early graft loss and delayed insulin independence. In a temporary hypoxic environment, intracellular processing of insulin release may be halted resulting in a quiescent period of low insulin secretion and reduced sensing of hyperglycemia until neurovascular networks mature. This phenomenon may not be critical to long-term outcomes if islets, stem cells or alternative cells require a prolonged period of engraftment and function, but does require adequate and effective blanket immunosuppression at least during this period, as it would be difficult to elucidate function impairment until there is detectable graft efficacy.

Embodiments of the present invention may provide an appropriate surrogate for clinical islet engraftment leading to long-term islet and insulin producing stem cell graft function. Additionally, embodiments of the present invention may comprise the use of imaging technologies to track and monitor graft survival and immunological response, such as real-time, non-invasive imaging technologies, such as photoacoustic ultrasound[34], which currently cannot be done with intraportal clinical islet transplantation.

In one embodiment, the transplant site methodology described herein may also be used in conjunction with optogenetics. For example, genetically modified secretory cells with a light sensitive ion channels, such as channelrhodopsin, can be engineered to secrete a specific protein, hormone or therapeutic agent simply by shining an appropriate wavelength of light over the subcutaneous cellular transplant[35]. Thus, by transplanting genetically engineered cells into the prepared transplant site, and photoactivating the cells, a selected protein, hormone or other therapeutic agent may be delivered to the host.

In addition, in one embodiment, this process affords the opportunity to study in a pre-clinical in vivo setting, cancer progression, growth and susceptibility to various chemotherapeutic agents. By implanting tumors directly resected from patients, for example a pancreatic tumor, into an animal such as a mouse, a personalized treatment can be potentially predicted based on animal's response to treatment. However, depending on tumor type, some tumors can be very hard to grow with engraftment rate as low as 20%. The cellular transplantation methods described herein may be used to transplant cancer cells to improve engraftment and survival for certain tumors that cannot be implanted by conventional methods; thus providing a model to test patient specific tumor sensitivity to chemotherapeutic agents, thereby directing subsequent clinical intervention.

EXAMPLES

The following examples are provided to exemplify embodiments of the invention, and are not intended to limit the claimed invention in any manner.

The following data demonstrates that a previously suboptimal, low oxygen tension, subcutaneous transplant site may be transformed into a densely vascularized space suitable for cellular transplantation and long-term graft survival.

Generally, diabetic mice were transplanted with 500 syngeneic islets into a prepared transplant site in a subcutaneous space in parallel to recipients of islets transplanted under the kidney capsule and naïve subcutaneous transplants. Islet transplanted renal subcapsular mice were able to reverse diabetes in 100% (n=10 of 10) of the recipients, whereas all diabetic recipients (n=10) transplanted with islets into the naïve subcutaneous space, failed to achieve normoglycemia. However, the prepared subcutaneous group, reversed diabetes in 91.3% (n=21 of 23) of the recipients transplanted and maintained normoglycemia for >100 days. This study demonstrated the ability to reverse diabetes by placing insulin-producing islets under the skin without the use of a permanent device, matrix or exogenous growth factors. This technique may be an appropriate surrogate for clinical islet engraftment leading to long-term islet and potential insulin producing stem cell graft function.

Example 1

Preparation of the Subcutaneous Space

Figure 2:
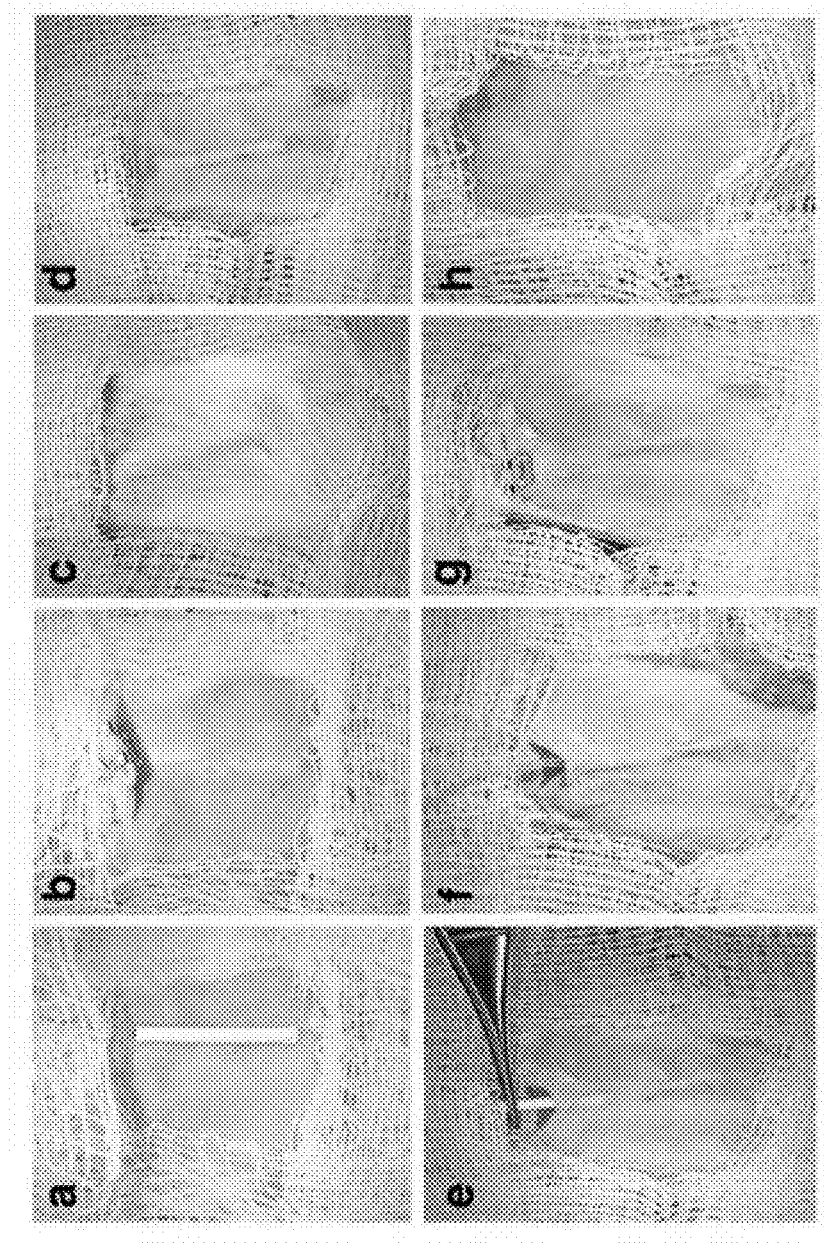
FIG. 2. shows a photographic overview of the subcutaneous transplant procedure. To create the transplant site a medical angiocatheter (a) is implanted under the skin (b). The implant is left under the skin (c-d) for a period of 3-6 weeks. Subsequent to the implant period, the angiocatheter is removed (e) creating a vascularized void where the islet transplant is infused (f). After the transplant incision is closed (g) the islet graft exhibited no visible profile post-transplant up to 100 days post-transplant (h).
Figure 10:
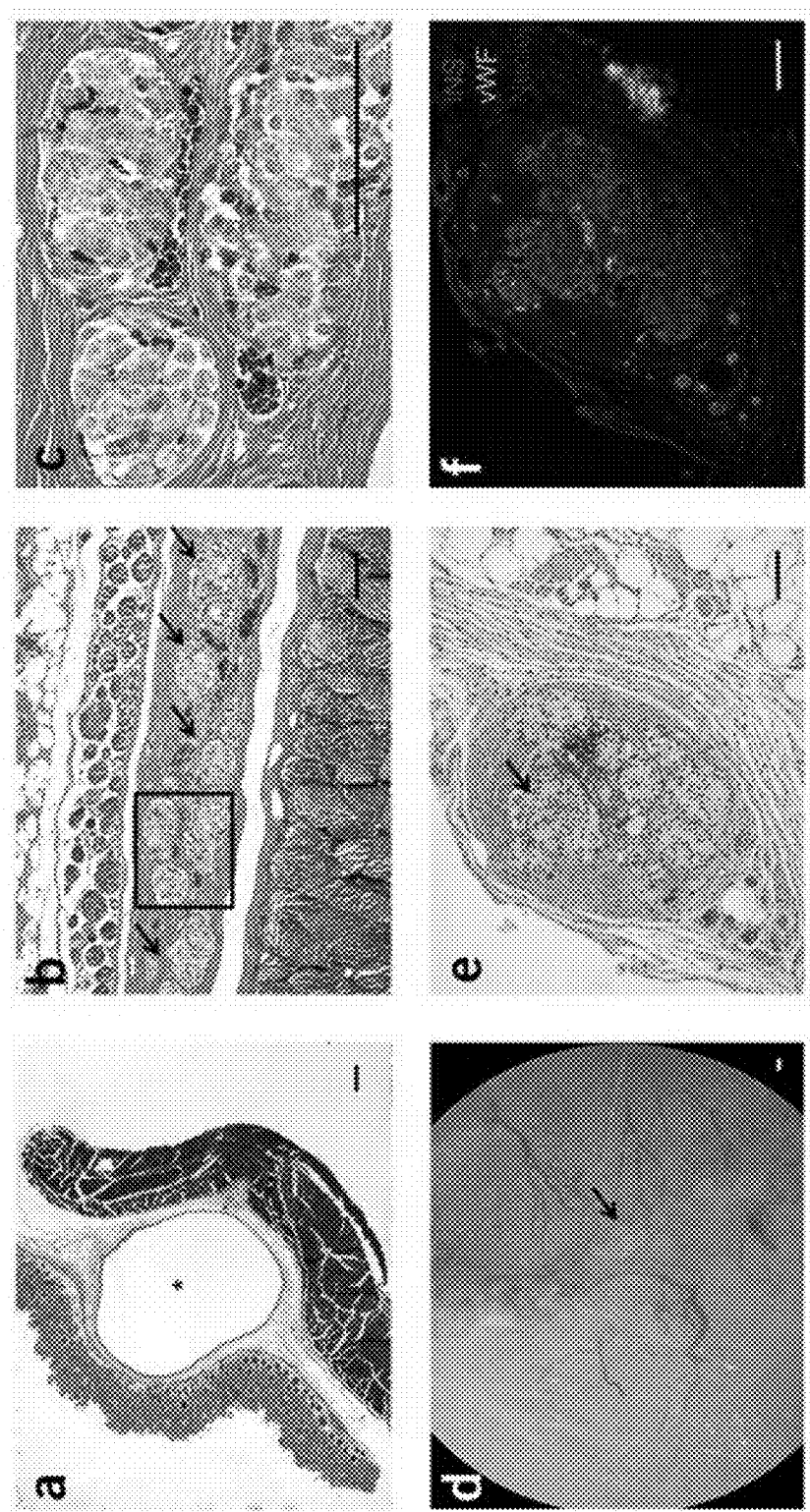
FIG. 10. Histological analysis of islets transplanted long-term into the subcutaneous 'deviceless' space. (a) Mason's trichrome staining illustrating the cross-section of the 'deviceless' site created four weeks post-catheter implantation. Cellular transplants are infused into the lumen generated subsequent to catheter removal (*). Collagen (blue, smooth muscle and erythrocytes (red) at 2×. (b) 10× and (c) 40× Mason's trichrome staining of a long-term islet graft (>100 days) within the 'deviceless' site, surrounded with collagen and blood vessels. Arrows indicate engrafted islets within a vascularized collagen scaffold. (d) Macroscopic image of the neovascularization penetrating the length of an islet graft within the subcutaneous 'deviceless' site. (e) Hematoxylin & eosin staining of an islet graft cross-section, 100 days post-transplant (10×). (f) Fluorescent staining of the same cross-section staining for insulin (red), blood vessels (green) and nuclei (blue) (10×). Scale bar represents 100 µm.

Three to six weeks prior to islet transplant, 2 cm segments of a 5 French textured nylon radiopaque angiographic catheter (Cook Medical, Indiana, USA) or a 6.5 French smooth silicone catheter (Cook Medical, Indiana, USA) was implanted subcutaneously into the lower left quadrant of 20-25 g male BALB/c mice (Jackson Laboratories, Canada) for mouse syngeneic islet transplant (FIG. 2(a)) or B6.129S7-Rag1$^{tm1Mom}$ immunodeficient mice for human islet transplants. A <1 cm lateral transverse incision was made caudal to the rib cage allowing for a small pocket to be created inferior to the incision line using blunt dissection. An adequate void (1 cm by 3 cm) was created. The catheter segment was implanted into the space such that the catheter engrafted parallel to the midline. The incision was closed with a surgical staple (Autoclip®, Becton Dickinson, Sparks, Md.) (FIG. 2(b)). Once implanted, the catheter became engrossed with blood proteins, leading to the formation of densely vascularized tissue, which exhibited a minimally visible profile (FIG. 2(c-d)). Removal of the implant revealed a vascularized lumen allowing for cellular transplant infusion (FIG. 1 and FIG. 10(a)).

Example 2

Proinflammatory Cytokine and Chemokines Measurements

A one-centimeter segment from both nylon and silicon catheter material was placed subcutaneously into the left lower quadrant of 20-25 g male BALB/c mice. Implanted catheters with surrounding skin and muscle tissue margins were explanted 24 hours, 1 week and 2 weeks post-implantation. Similarly, tissue dissections were retrieved from the abdomen of non-implanted mice, serving as background cytokine and chemokine control specimens. The respective catheter segments were carefully removed from the surrounding tissue, yielding a hollow void encompassed by a vascularized matrix. Tissue samples were immediately placed in pre-weighed microcentrifuge tubes. The tissue weights were recorded, then subsequently flash frozen with liquid nitrogen and stored at −80° C. prior to conducting the cytokine and chemokine proinflammatory analysis. Once all tissue samples from respective implantation period were collected and frozen, 1 mL of lysis buffer (0.15 M NaCl, 1 mM Tris-HCl, 0.1% SDS, 0.1% Triton X-100, 20 mM Sodium deoxycholate, 5 mM EDTA) per 200 mg of tissue was added to the tissue containing microcentrifuge tube. Each tissue sample was homogenized (PowerGen, Fisher Scientific, Ontario, Canada) on ice for 30 sec×2 replications. Samples were then sonicated (VirSonic, VirTis, NY, USA) with 10 quick pulses while on ice. Lysed tissue samples were centrifuged at 14,000 rpm for 10 min at 4° C. to remove cellular debris. The resulting supernatant was collected and placed in a microcentrifuge tube containing 10 µL of a protease inhibitor cocktail (Sigma-Aldrich Canada Co., Oakville, ON, Canada) per 1 mL of lysate (1:100). Peri-implant cytokine and chemokine (IL-1β, IL-12p70, IFN-γ, IL-6, KC/GRO, IL-10 and TNF-α) measurements were conducted using a Multi-Spot Mouse ProInflammatory 7-Plex Ultra-Sensitive kit (Meso Scale Discovery®, Gaithersburg, Md., USA) requiring 25 µL of lysate/replicate and analyzed on a SECTOR Imager (Meso Scale Discovery®, Gaithersburg, Md., USA).

Acutely post-implant, blood-material interactions, platelets and clots release chemoattractants including transforming growth factor (TGF-β) and interleukin-1β (IL-1β), which home macrophages into the wound or implant site[17, 29]. Accordingly, the potent proinflammatory cytokine IL-1β, was significantly greater in the nylon implanted animals (80.2±2.3 pg/g-tissue) compared to silicone implanted animals (8.70±2.60 pg/g-tissue) and control animals (2.29±0.66 pg/g-tissue) 24 hours post-implant (p<0.001 and p<0.001, respectively, FIG. 9A(a). One-week post-implant, IL-1β levels remained considerably elevated in nylon catheter tissues compared to controls (295.7±61.8 pg/g-tissue vs. 2.29±0.66 pg/g-tissue, p<0.05); however there was no discernable difference in silicone catheter tissue segments compared to nylon segments at this time point (330.8±110.9 pg/g-tissue, FIG. 9A(b). By two weeks post-implant, peri-catheter IL-1β secretion returned to control levels in both catheter groups (FIG. 9A(c)).

Activated macrophages secrete the cytokine IL-6 during wound healing, which we detected in peri-implant tissues 24 hours post-implant. At this time point, both the nylon and silicone catheters elicited the secretion of significant levels of IL-6 compared to control samples; however these levels did not differ from each other (501.8±34.0 pg/g-tissue and 385.3±117.2 pg/g-tissue, respectively vs. 115.2±14.2 pg/g-tissue controls, p<0.05) (FIG. 9A(d)0. One-week post-implant IL-6 levels returned to control levels (FIG. 9A(e)), and were sustained at the two-week time period (FIG. 9A(f)).

Figure 9A:
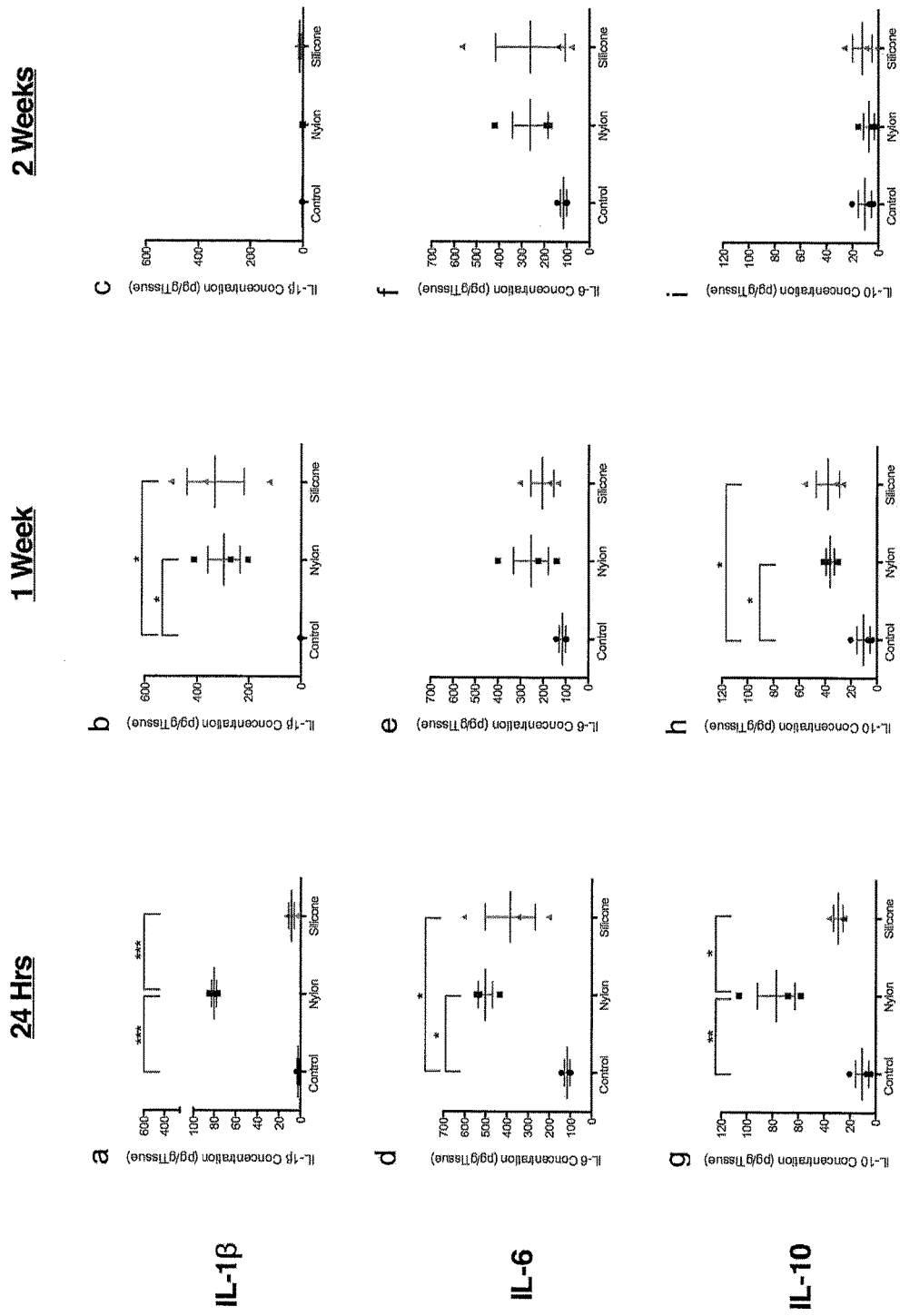
FIGS. 9A and 9B. The proinflammatory response elicited by both nylon (blue) and silicone (red) compromised angiocatheters when implanted subcutaneously for 24 hours, 1 week and 2 weeks. (a-c) The peri-implant concentrations of IL-1β, (d-f) IL-6, (g-i) IL-10, (j-l) TNF-α, (m-o) KC/GRO, and (p-r) IL-12p70. Data points represent mean±s.e.m for pg/g-tissue, $*p<0.05$, $p<0.01$, $*p<0.001$ (n=3/time point). Analysis of variance calculated by one-way Anova and Newman-Keuls post-hoc testing.

In addition, IL-10 levels, secreted by macrophages, were significantly greater in the nylon-implanted animals after 24 hours (77.2±14.4 pg/g-tissue) compared to silicone (29.3±3.6 pg/g-tissue) and control animals (10.4±5.1 pg/g-tissue) (p<0.05 and p<0.01, respectively, FIG. 9A(g). One-week post-implant, IL-10 secretion continued to be elevated in nylon catheter tissues compared to controls (36.3±3.2 pg/g-tissue vs. 10.4±5.1 pg/g-tissue, p<0.05); however, there was no observed difference in silicone catheter tissue segments (38.2±9.0 pg/g-tissue; FIG. 9A(h). Peri-catheter IL-10 quantities returned to control measurements in both catheter groups by 2 weeks post-implant (FIG. 9A(i)).

In the context of the foreign body reaction, tumour necrosis factor alpha (TNF-α) is secreted by macrophages as a means to recruit additional peripheral macrophages to the implant site[17]. In our study, TNF-α levels did not achieve significant levels compared to control tissue segments until 1 week post-implant for both materials; with no detectable difference between the catheter groups (nylon: 46.1±8.4 pg/g-tissue, silicone: 33.2±8.46 pg/g-tissue vs. control: 2.04±0.42 pg/g-tissue, p<0.01 and p<0.05 respectively) (FIG. 9B(j-k)). Basal levels of TNF-α were measured 2 weeks post-implant in both implant groups (FIG. 9B(l)).

Figure 9B:
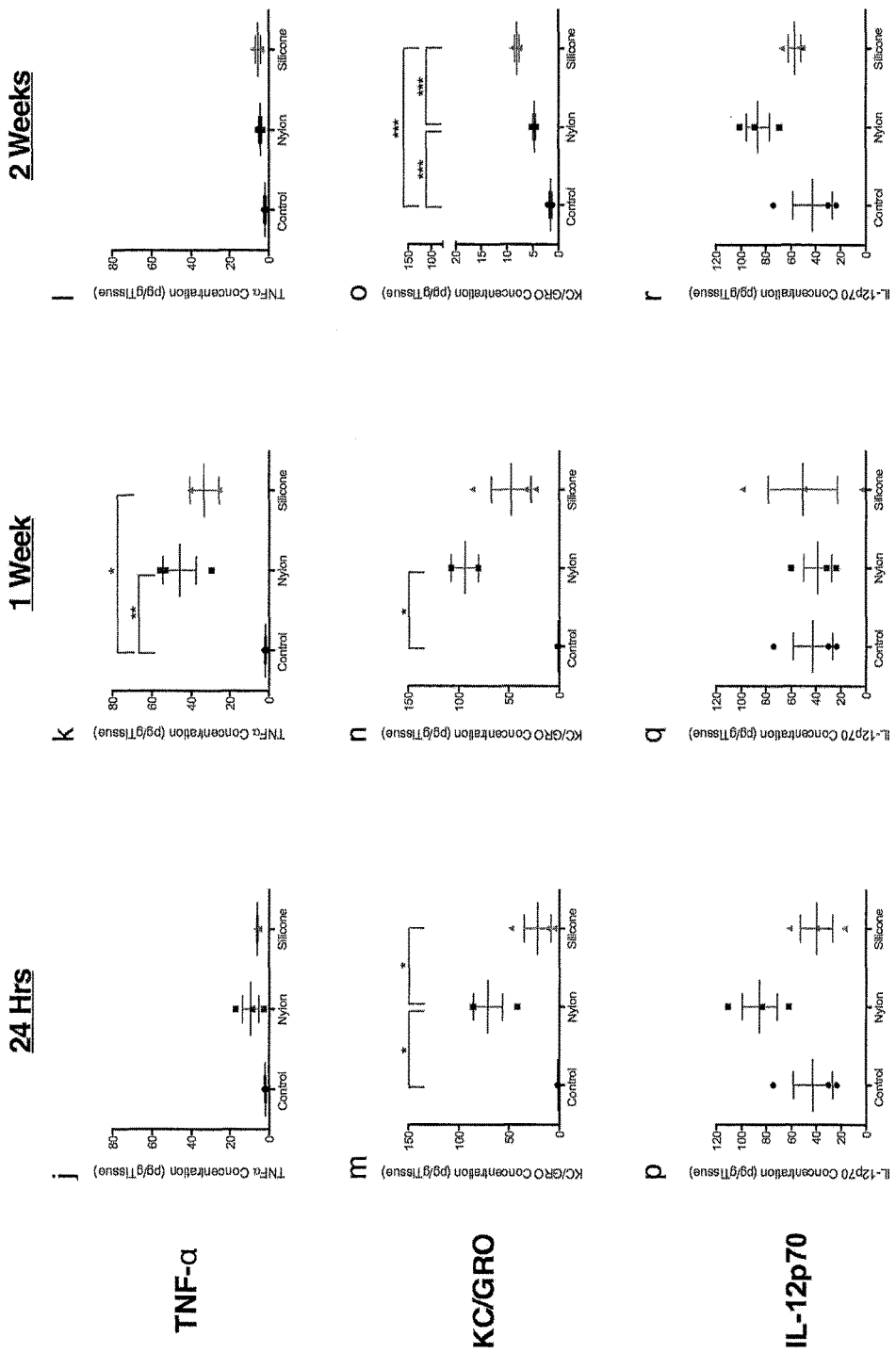

Tissue levels of the chemokine KC/GRO for neutrophil recruitment, was significantly greater in the nylon-implanted host (71.0±14.7 pg/g-tissue) compared to silicone (21.6±13.2 pg/g-tissue) and control tissue samples (1.56±0.30 pg/g-tissue) 24 hours post-implant (p<0.05 and p<0.05, respectively, FIG. 9B(m). Since neutrophils are one of the initial immune cells present at a wound site, it is not surprising that we observed significant KC/GRO levels 24 hours post-implant. However, it is of note that only the textured nylon-catheter stimulated such an acute secretion of KC/GRO, which could in part explain differences in the biomaterials downstream ability to promote neovascularization and collagen deposition. One-week post-implant, only the nylon implanted tissues illustrated higher concentrations of KC/GRO compared to control tissue samples (93.9±13.7 pg/g-tissue vs. 1.56±0.30 pg/g-tissue, p<0.05) (FIG. 9B(n)).

By 2 weeks post-implant, silicone catheters elicited the greatest secretion levels compared to nylon and control tissue specimens (silicone: 8.14±0.42 pg/g-tissue; nylon: 4.72±0.27 pg/g-tissue; control: 1.56±0.30 pg/g-tissue, p<0.001 and p<0.001, respectively) (FIG. 9B(o)).

Despite a lack of statistical significance, trends suggest that the nylon-based catheter stimulates quantifiably more IL-12p70 compared to silicone-based biomaterials at 24 hours and 2 weeks post-implant (FIG. 9B(p-r)). IFN-γ was analyzed, however it was not detected in any samples.

The cytokine and chemokine profile timing are similar to the observations summarized by Anderson et al, where hydrophobic biomaterials were implanted subcutaneously[17]. Our data shows that the textured nylon catheter was able to significantly induce greater levels of cytokines and chemokines compared to the silicone based biomaterials.

Example 3

Mouse Pancreatectomy and Islet Isolation

Pancreatic islets were isolated from 8 to 12 week old male BALB/c mice. Animals were housed under conventional conditions having access to food and water ad libitum. The care for all mice within the study was in accordance with the guidelines approved by the Canadian Council on Animal Care. Prior to pancreatectomy, the common bile duct was cannulated with a 27 G needle and the pancreas was distended with 0.125 mg/mL cold Liberase TL Research Grade enzyme (Roche Diagnostics, Laval, QC, Canada) in Hanks' balanced salt solution (Sigma-Aldrich Canada Co., Oakville, ON, Canada). Islets were isolated by digesting the pancreata in a 50 mL tube placed in a 37° C. water bath for 14 minutes with light shaking. Subsequent to the digestion phase, islets were purified from the pancreatic digests using histopaque-density gradients (1.108, 1.083 and 1.069 g/mL, Sigma-Aldrich Canada Co., Oakville, ON, Canada).

Example 4

Human Islet Isolation

Pancreata from multi-organ deceased confirmed consent donors were procured post-aortic cross-clamp and infused with preservation solutions. Islets from two separate human islet preparations were isolated implementing a modified Ricordi's technique[19, 20]. In short, the pancreas was distended with collagenase blend solution and digested in a Ricordi chamber. When islets were adequately dissociated from surrounding acinar tissue, the pancreatic digest was collected. Islets were purified from the pancreatic digest using a continuous density gradient on a cell processor centrifuge (Model 2991, Cobe, Lakewood, Co, USA). All human islet preparations were processed with intent for clinical transplantation. Human islets were cultured overnight in CMRL-1066 media supplemented with insulin selenium-transferrin and insulin-like growth factor-1 at 22° C. prior to transfer to the laboratory for experimentation.

Example 5

Diabetes Induction and Islet Transplantation

Three to five days prior to transplantation, implanted mice were rendered diabetic by chemical induction through the administration of an intraperitoneal injection of streptozotocin at 185 mg/kg in acetate phosphate buffer, pH 4.5 (Sigma-Aldrich Canada Co., Oakville, ON, Canada). Animals were considered diabetic when their blood glucose levels exceeded a pre-established value of 15 mmol/L (350 mg/dL) for 2 consecutive daily readings. At the time of transplantation, 500 mouse islets±10% with purity of 90%±5% or 2000 human islet equivalents (IE) were aspirated into polyethylene (PE-50) tubing using a micro-syringe, and centrifuged into a pellet suitable for transplantation. Islet preparations were distributed randomly to all three transplant recipient groups: Deviceless (DL), kidney capsule (KC) or subcutaneous alone. DL recipient mice were maintained under anesthesia with inhalant isoflurane, and placed in a supine position. A field surrounding the implanted catheter was prepared by shaving and surface disinfected with soap scrub, povidone-iodine (Betadine, Purdue Pharma, Oakville, ON, Canada) and isopropyl alcohol. Cranial to the superior edge of the implanted catheter, a small (1 cm) incision was made to gain access to the catheter. The tissue matrix engrossing the superior margin of the catheter was carefully dissected in order to remove the catheter (FIG. 1 and FIG. 2(e)). The PE-50 tubing containing the islet preparation was subsequently placed within the vascularized lumen, and the islets were expelled into the void using a micro-syringe (FIG. 1, FIG. 10(a) and FIG. 2(f)). The incision was closed with a surgical staple (Autoclip®, Becton Dickinson, Sparks, Md.) (FIG. 2(g)). Prior to recovery, recipients received a 0.1 mg/kg subcutaneous bolus of buprenorphine. Control animals were rendered diabetic and transplanted with 500 mouse islets/recipient as described above, however the islets were infused into the subcutaneous space alone (no prevascularization or catheter implant). In addition, a subset of diabetic animals was transplanted with 500 mouse islets/recipient under the kidney capsule (KC), the standard site for rodent islet transplantation. For all experiments islets were pooled, batched and transplanted in random allocation to either the DL subcutaneous or KC sites. To facilitate this transplant, a left lateral paralumbar subcostal incision was made and the left kidney was delivered into the wound. The renal capsule was incised and space was made under the capsule to allow transplantation of the islets through the tubing. The subcostal incision was closed in two layers. The efficacy of mouse islets transplanted into our subcutaneous DL site to reverse diabetes was compared to the engraftment efficacy of islets transplanted subcutaneously alone or under the renal subcapsule.

Example 6

Evaluation of Islet Graft Function

Human islets transplanted into a prepared DL subcutaneous space will survive and remain functional long-term (>100 days) in mice. Succeeding a 3-6 week implant period, recipient mice were rendered diabetic and transplanted with 500 syngeneic islets into a prepared DL space created by a nylon-based catheter. In parallel, two additional islet transplant groups were compared: 1) under the kidney capsule (KC) and, 2) subcutaneous alone (SubQ). In addition, a group of immunodeficient diabetic mice were transplanted with 2,000 human IE into the prepared DL space created by the nylon catheter.

Figure 3:
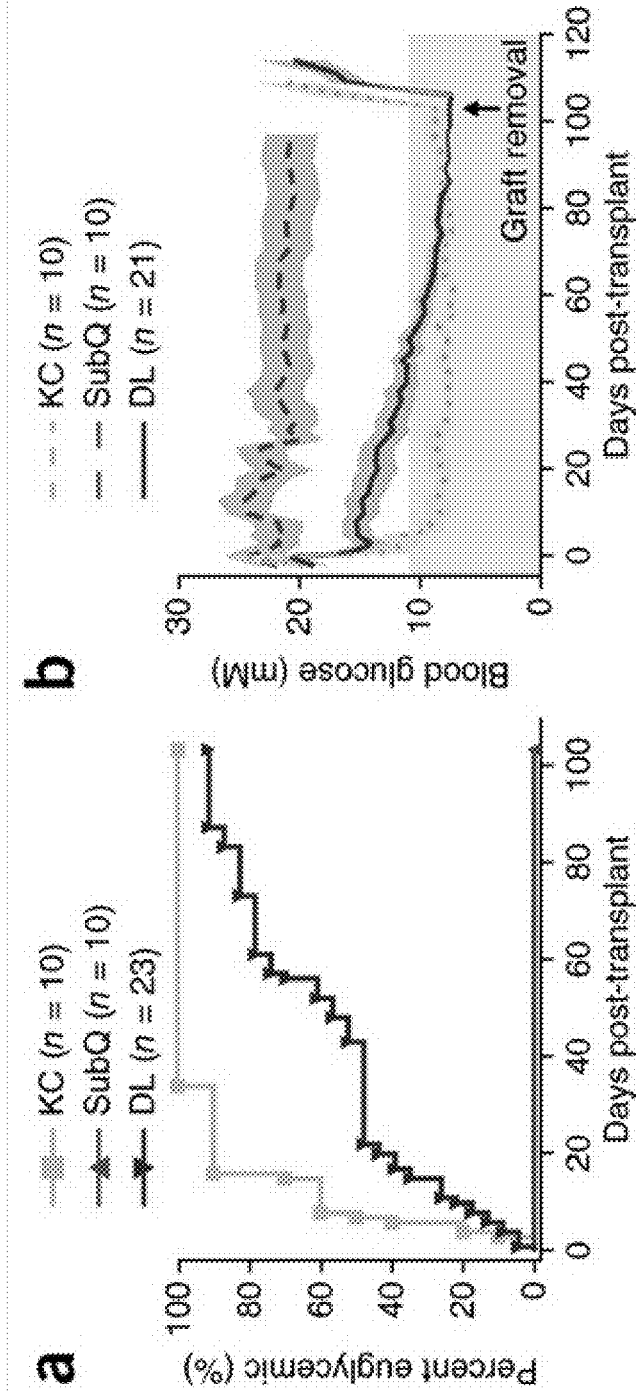
FIG. 3. Long-term syngeneic islet graft function transplanted into a "deviceless" transplant site in a subcutaneous space. (a) Reversal of diabetes rates, percent euglycemia, between islet-kidney capsule (KC) recipients and 'deviceless' (DL) recipients were similar 100 days post-transplant, with KC recipients reversing diabetes earlier compared to DL, (p=0.001, Log-rank, Mantel-cox test). (b) Non-fasting blood glucose measurements, post-transplant. Both KC and 'deviceless' islet recipients maintained normoglycemia until the time of graft retrieval (arrow—105 days), at which point recipients reverted back to pre-transplant hyperglycemic state. Islets transplanted subcutaneously alone failed to provide glycemic control to the recipient (SubQ-red, n=10). Shaded area represents a non-fasting physiological range ($<11.1$ mM). Data points represent blood glucose mean±s.e.m.

As expected, islets transplanted under the KC were able to reverse diabetes in 100% (n=10 of 10) of the recipients (FIG. 3(a)), within 11.5±2.9 days post-transplant (FIG. 3(b)). Also, as predicted all diabetic recipients transplanted with islets into the naïve subcutaneous space, failed to achieve glucose control (n=0 of 10), at any time-point post-transplant (FIG. 3(a,b)). However, when the subcutaneous site in diabetic mice was prepared in accordance with our invention, the ensuing islet infusion within the void created by the catheter withdrawal, reversed diabetes in 91.3% (n=21 of 23) of the recipients transplanted (FIG. 3(a)), within 35.4±6.0 days post-transplant (FIG. 3(b)). This represents a significant improvement compared to SubQ alone transplants (p<0.0001 log-rank).

Figure 5:
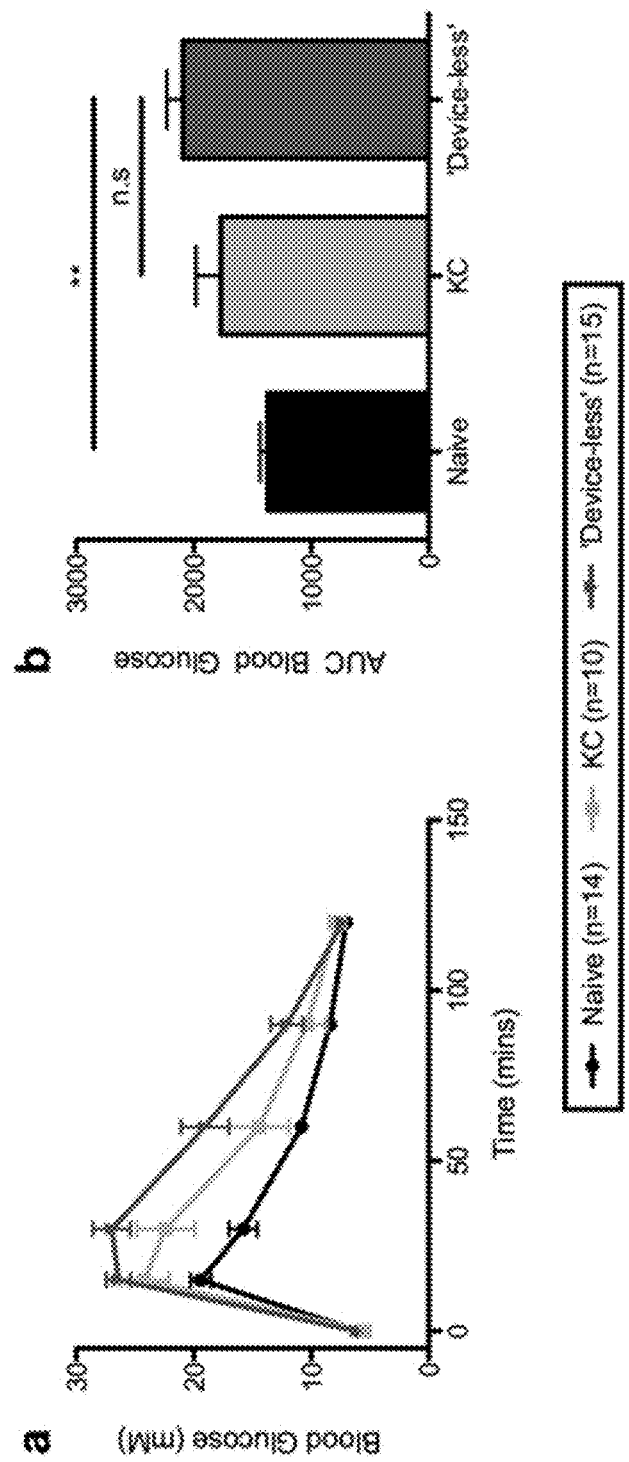
FIG. 5. Intraperitoneal glucose tolerance test of syngeneic mouse islets transplanted under the kidney capsule or into the subcutaneous 'deviceless' site, 100 days post-transplant, (a) Blood glucose post-dextrose bolus (b) area under the curve (AUC) analysis did not differ between the kidney capsule (KC, n=10) and 'deviceless' (n=15) recipients ($p>0.05$, one-way Anova-Newman-Keuls post-hoc test). Naïve represents non-diabetic, non-transplant BALB/c mice (n=14), which were more tolerance to the metabolic test than the 'deviceless' islet recipients (**$p<0.01$, $p>0.05$, one-way Anova-Newman-keuls post-hoc test). Mice were administered 3 mg/kg 50% dextrose i.p. Blood glucose measurements were monitored at t=0, 15, 30, 60, 90 and 120 minutes. Data points represent blood glucose mean±s.e.m.

After normoglycemia had been maintained >100 days post-transplant, recipients were challenged with an intraperitoneal glucose bolus to assess glucose tolerance (FIG. 5(a)). Islet grafts from both the KC (n=10) and DL (n=15) transplanted animals were able to respond to the large influx of glucose and rapidly release insulin, returning the animals to their pre-glucose bolus normoglycemic levels. KC and DL transplanted islets were able to engraft in a similar fashion, evidenced through their comparable blood glucose response, AUC (KC: 1771-212 vs. DL: 2095±138, n.s) (FIG. 5(b)). The naïve non-diabetic group, as expected, responded the most robustly to the metabolic test compared to the DL recipients (AUC naïve: 1375±62, p<0.01) (FIG. 5(b)).

Figure 7:
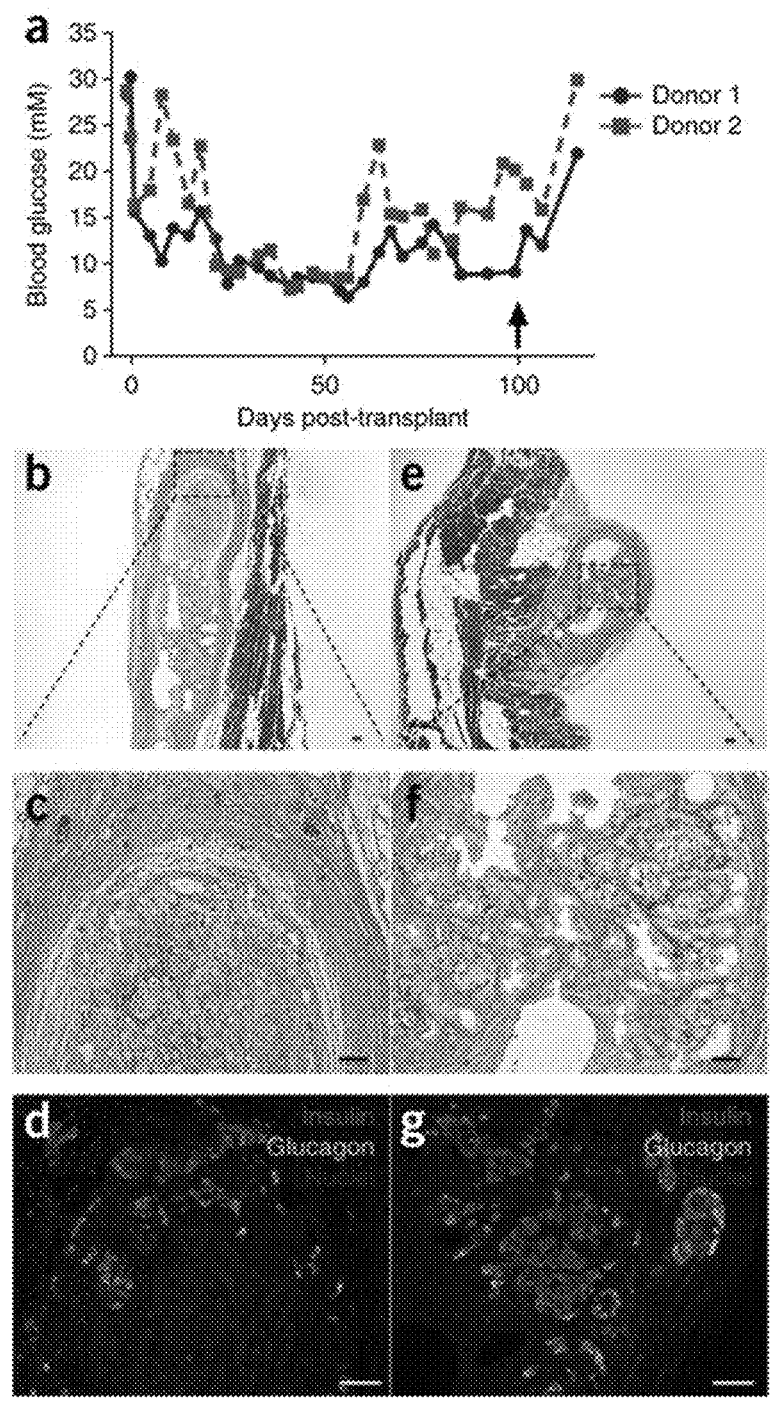
FIG. 7. Long-term human islet graft function transplanted into the 'deviceless' subcutaneous space. (a) Non-fasting blood glucose measurements, post-transplant maintained normoglycemia until the time of graft retrieval (arrow), at which point recipients reverted back to pre-transplant hyperglycemic state. (b,e) 2× and (c,f) 20× Mason's trichrome staining of a long-term islet graft (>100 days) within the 'deviceless' site, surrounded with collagen and blood vessels. (d,g) Fluorescent staining of the same cross-section staining for insulin (red), glucagon (green) and nuclei (blue) (20×). Scale bar represents 100 µm.

These data were mirrored when human islets were transplanted into DL space in diabetic mice (FIG. 7(a)), which were supported in a vascularized collagen matrix and stained positive for insulin and glucagon>100 days post-transplant (FIG. 7(b-g)).

To confirm graft dependent euglycemia, animals with functional grafts had their islet transplants explanted by nephrectomy or subcutaneous graft excision. All animals reverted back to a pre-transplant hyperglycemic state within one week of islet-graft bearing retrieval (FIGS. 3(b) and 7(a)). Islet graft function was assessed through non-fasting blood glucose measurements, using a portable glucometer (OneTouch Ultra 2, LifeScan, Canada) three times per week following islet transplantation, in all groups transplanted. Reversal of diabetes was defined as two consecutive readings less than, a pre-established value of, 11.1 mmol/L (in accordance with the American Diabetes Association) and maintained until the completion of the study.

In addition, glucose tolerance tests were conducted 60 or 100 days post-transplant on mice, as a means to further assess the metabolic capacity of the islet grafts in response to a glucose bolus, thus mimicking a postprandial stimulus. Animals were fasted overnight prior to receiving an intraperitoneal glucose bolus (3 g/kg). Blood glucose levels were monitored at 0, 15, 30, 60, 90 and 120 minutes post injection, allowing for area under the curve (AUC-blood glucose) to be calculated and analyzed between transplant groups.

Example 7

Evaluation of Foreign Body Material on Subsequent Islet Graft Function

The surface characteristics of an implant directly modulate the foreign body response; which we believe translates to an in vivo relevance when creating the DL site. DL subcutaneous transplant sites were prepared using both smooth silicone and textured nylon catheters 3-6 weeks prior to diabetes induction and subsequent mouse islet syngeneic transplant. The efficacy of islets to reverse diabetes in four different transplant sites was evaluated. Islet transplant groups consisted of 1) under the KC, 2) silicone DL, 3) nylon DL, and 4) SubQ alone. The post-transplant non-fasting glycemic values, for each group, were monitored for 60 days followed by an intraperitoneal glucose tolerance test.

Figure 4:
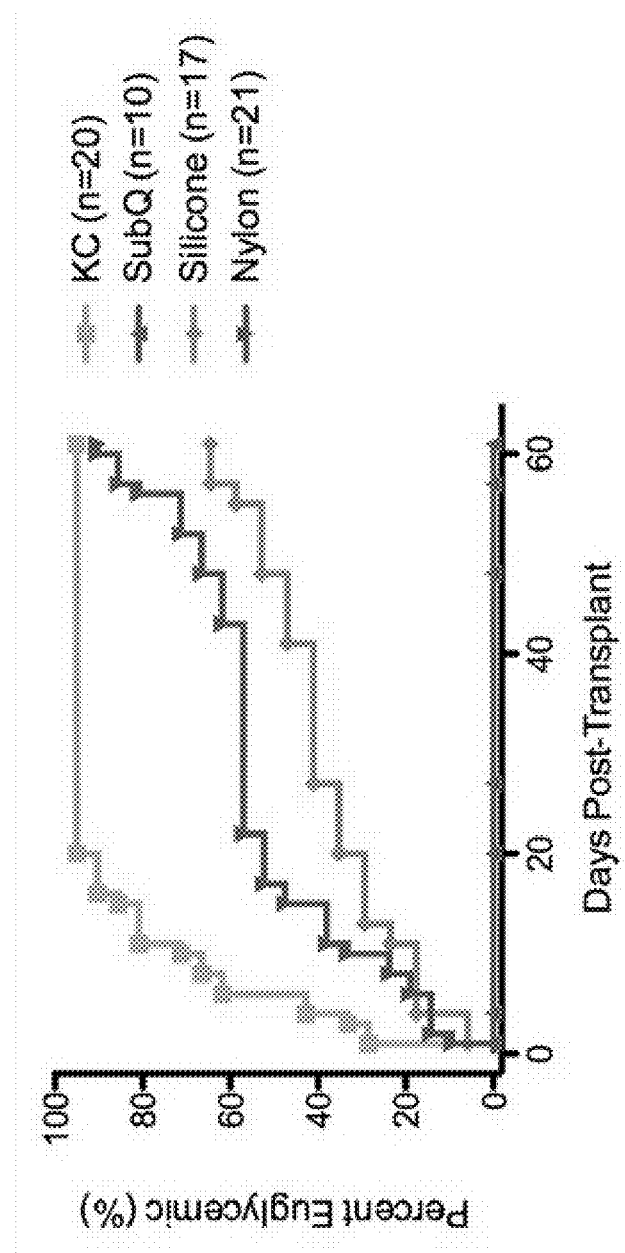
FIG. 4. The rate of diabetes reversal, percent euglycemia, in mouse recipients of a syngeneic islet transplant. Glycemic control, measured by twice weekly non-fasting blood glucose levels, was monitored for 60 days post-islet transplant in chemically induced (STZ) diabetic mice. Reversal of diabetes was defined as a maintained non-fasting blood glucose level of $<11.1$ mM. Transplant recipients received 500 BALC/c islets. Islet transplant groups consisted of: kidney capsule (KC, n=20), subcutaneous alone (SubQ, n=10), 'deviceless' silicone (Silicone, n=17) and 'deviceless' nylon (Nylon, n=21). Data points represent blood glucose mean±s.e.m.

As expected, by three weeks post-transplant 95.2% (n=19 of 20) of the KC recipients became euglycemic and remained so for the 60-day study period (FIG. 4). Also, as predicted, animals transplanted SubQ alone failed to achieve glycemic control (n=0 of 10), similar to the long-term study. Interestingly, 35.3% (n=6 of 17) animals transplanted with islets subcutaneously using a silicone DL site became normoglycemic three weeks post-transplant, and by the 60-day endpoint, 64.7% (n=11 of 17) of the recipients reversed diabetes. In contrast, three weeks post-islet transplant into the subcutaneous nylon DL location, 57.4% (n=12 of 21) of the recipients became euglycemic. Furthermore, by the 60-day time point, 90.5% (n=19 of 21) of the nylon DL transplanted animals reversed diabetes, mirroring the results of the standard islet-KC group (FIG. 4).

Figure 6:
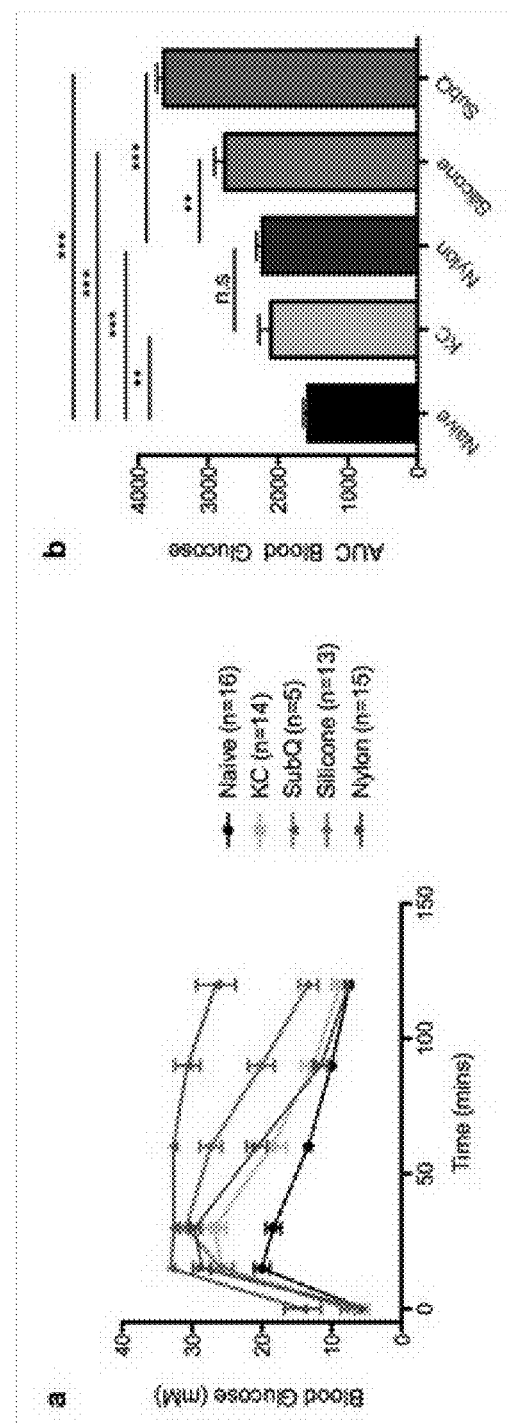
FIG. 6. Intraperitoneal glucose tolerance test of syngeneic mouse islets transplanted under the kidney capsule or into the subcutaneous 'deviceless' (DL) site, 60 days post-transplant. (a) Blood glucose post-dextrose bolus (b) area under the curve (AUC) analysis did not differ between the kidney capsule (KC, n=14) and nylon-DL (n=15) recipients ($p>0.05$ one-way Anova-Newman-keuls post-hoc test). Nylon-DL recipients were more tolerant to a glucose challenge than silicone-DL (n=13, $p<0.01$ one-way Anova-Newman-keuls post-hoc test). Islets transplanted under the skin alone, (SubQ, n=5), were intolerant to the glucose challenge compared to nylon-DL recipients (*$p<0.001$ one-way Anova-Newman-keuls post-hoc test). Naïve represents non-diabetic, non-transplant BALB/c mice (n=16), which were more tolerance to the metabolic test than the kidney capsule and 'deviceless' islet recipients ($p<0.01$ and *$p<0.001$ respectively one-way Anova-Newman-keuls post-hoc test). Mice were administered 3 mg/kg 50% dextrose i.p. Blood glucose measurements were monitored at t=0, 15, 30, 60, 90 and 120 minutes. Data points represent blood glucose mean±s.e.m.

The KC (n=14) and nylon DL (n=15) transplanted animals, demonstrated similar responses to the challenge by rapidly returning to normoglycemia subsequent to an intraperitoneal bolus of glucose (FIG. 6(a)). As a result there was no difference in these transplant groups blood glucose AUC (FIG. 6(b)). The silicone DL recipients (n=13) demonstrated glucose intolerance during the metabolic challenge, compared to the nylon group; this made evident by significantly greater blood glucose AUC (p<0.01, FIG. 6(b)). Islets transplanted SubQ alone (n=5) failed to respond to the glucose tolerance test. This was reflected in a significantly elevated blood glucose AUC compared to nylon DL recipients (p<0.001, FIG. 6(b)).

These data demonstrate that the surface properties of a biomaterial significantly impact the in vivo efficacy of creating a suitable subcutaneous microenvironment for cellular engraftment, complementing the proinflammatory observations. The nylon-based catheter is a more efficacious biomaterial than silicon, in creating the subcutaneous DL site. Moreover, these findings validate that islets transplanted under the skin, via the methods described herein can indeed function well, restoring glycemic control in a similar degree to the pre-clinical standard route.

Example 8

Long-Term Islet Graft Retrieval

To confirm graft dependent euglycemia, and to eliminate residual or regenerative native pancreatic beta cell function, animals with functional grafts had their islet transplants explanted by either nephrectomy or subcutaneous graft excision. Renal subcapsular islet transplant recipients were placed under anesthesia, and their graft-bearing kidney was exposed. A LT200 Ligaclip (Johnson & Johnson, Inc., Ville St-Laurent, QC, CA) was used to occlude the renal vessels and the ureter at the pedicle. The left kidney was dissected and the explanted graft preserved for immunohistochemistry in 10% formalin. Likewise, the subcutaneous islet grafts within the DL transplanted animals, which exhibited no visible profile post-transplant (FIG. 2(h)), were carefully removed by excising a small margin of the abdominal skin and musculature containing the islet graft. Following islet-graft removal non-fasting blood glucose measurements were monitored for the subsequent 7 days to observe a return to hyperglycemia, confirming post-transplant graft function.

Example 9

Histological Assessment

Immunofluorescence was used to identify endothelial cells for the assessment of vascularization using anti-von Willebrand factor (vWF) antibody and anti-insulin and anti-glucagon antibodies to identify the presence of pancreatic β-cells and α-cells, respectively. Briefly, following deparaffinization and antigen heat retrieval, the graft sections were washed with phosphate buffered saline supplemented (PBS) with 1% goat serum, followed by blocking with 20% goat serum in PBS for 30 minutes. The sections were treated with a primary antibody of guinea pig anti-pig insulin (Dako A0564) diluted 1:100 (PBS with 1% goat serum), rabbit anti-pig von Willebrand factor (Dako A0082) diluted 1:400 (PBS with 1% goat Serum) and or rabbit anti-glucagon (Abcam) diluted 1:200 (PBS with 1% goat serum) for 2 hours at 4° C. Samples were rinsed with PBS with 1% goat serum followed by secondary antibody treatment consisting of goat anti-guinea pig (Alexa 568) diluted 1:500 (PBS with 1% goat serum), and goat anti-rabbit (Vector Fl-1000) diluted 1:500 (PBS with 1% goat serum) for 30 minutes at room temperature. Samples were rinsed with PBS and counter stained with DAPI in anti-fade mounting medium (ProLong®, LifeTechnologies). Using a fluorescent microscope, the resulting microphotographs were taken using the appropriate filter with AxioVision imaging software. In addition, to assess the incorporation of vascularized collagen tissue into surrounding the DL islet-grafts, representative sections were stained with hematoxylin/eosin and Masson's trichrome.

Figure 8:
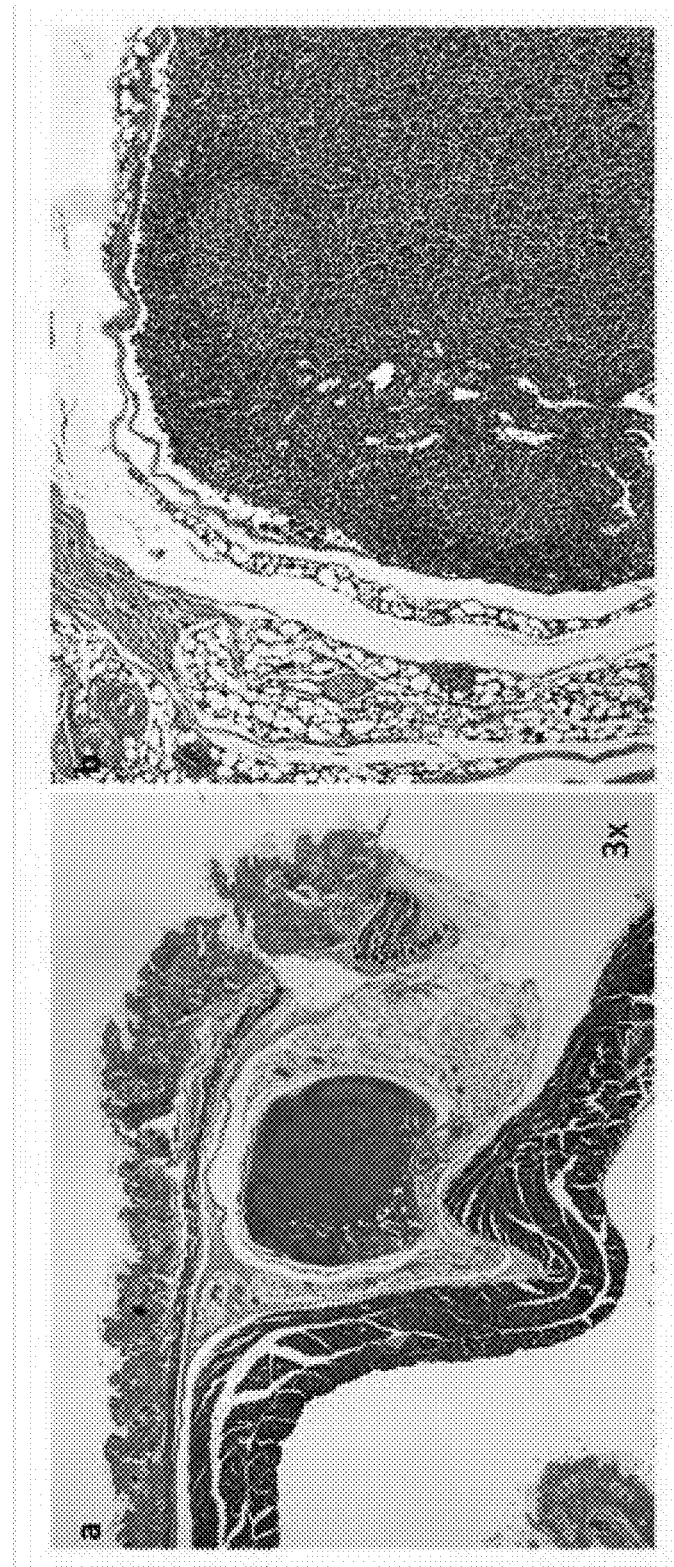
FIG. 8. Immunohistochemistry of a syngeneic islet graft transplanted into an unmodified (naïve) subcutaneous space 40 days post-transplant. Mason trichrome staining of cross-section of a subcutaneous islet graft at 3× (a) and 10× (b) magnification revealing robust inflammation and graft loss.

Upon histological analysis of explanted islet grafts within the DL site, islets were enveloped within a vascularized collagen scaffold between the skin and musculature (FIGS. 7(b-g) and 10(b,c)), in contrast to islets transplanted into the naïve subcutaneous space, which elicited a robust inflammatory response (FIG. 8(a,b)). At the time of graft retrieval, vascular networks were visible macroscopically, penetrating the islet tract created by the catheter. Of note, capillary networks were isolated to the DL area, as margins medial and lateral to the islet graft were typically avascular (FIG. 10(d)). The islets within the DL space (FIG. 10(e)), stained positive for insulin, in addition to endothelial cells of new microvessels (FIG. 10(f)). These data highlight the fact that a once hypoxic and cytotoxic microenvironment can be transformed into a suitable surrogate transplant site.

Example 10

Statistical Analysis

Non-fasting blood glucose and proinflammatory data are represented as the mean±standard error of mean (SEM). Sample size calculations were based on reversal of glycemia rates in control mice with islets placed subcutaneously (0%) vs. a projected estimate of 60% engraftment in the device-less, pre-vascularized site (Sample size n=20 or more per group; alpha 5%, power 100%) Blood glucose AUC analysis for glucose tolerance test data was conducted through non-parametric ANOVA using GraphPad Prism (GraphPad Software, La Jolla, Calif., USA). Newman-Keuls post-hoc tests were used following the analysis of variances. Kaplan-Meyer survival function curves were compared using the log-rank statistical method. P<0.05 was considered significant.

Example 11

Insulin Producing Stem Cells Transplanted in the DL Site Reverse Diabetes

Human derived insulin producing stem cells (IPS) transplanted into a prepared DL subcutaneous space will survive, differentiate and reverse diabetes in immunodeficient mice. Succeeding a 3-6 week implant period, using a 5.0 French nylon angiocatheter, recipient mice were rendered diabetic and transplanted with 10-40 microliters of IPS.

Figure 11:
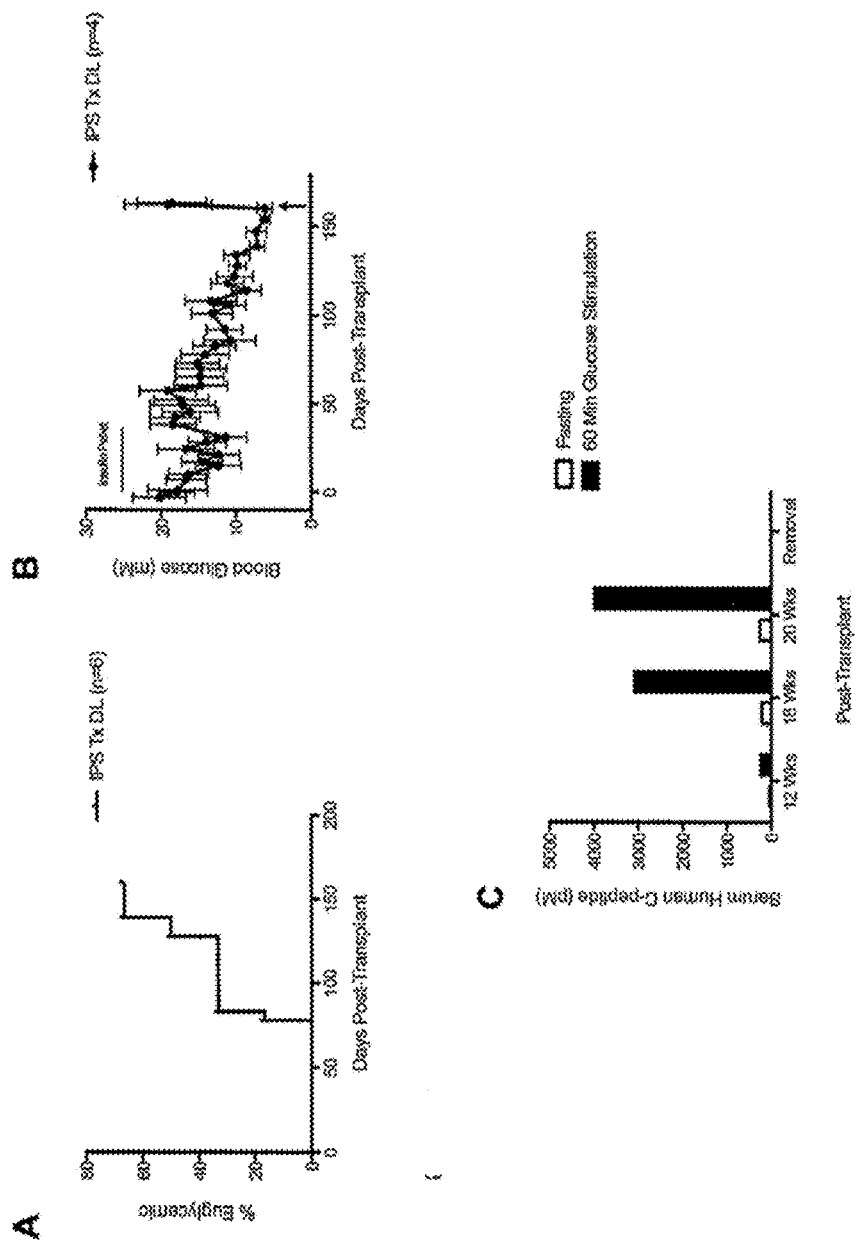
FIG. 11. Insulin producing stem cells (IPS) transplanted diabetic mice. (A) The rate of diabetes reversal, percent euglycemia, in mouse recipients of insulin producing stem cells (IPS) transplant into the DL site (n=6). (B) Recipients that demonstrated glycemic control (n=4), measured by twice weekly non-fasting blood glucose levels, was monitored for 160 days post-IPS transplant in chemically induced (STZ) diabetic mice. Normoglycemia was maintained until the IPS transplant was excised (arrow), returning the recipients to a pre-transplant hyperglycemic state. (C) Fasting and stimulate serum human C-peptide was measured at 12, 18 and 20 weeks post-transplant and following the removal of the IPS transplant. Reversal of diabetes was defined as a maintained non-fasting blood glucose level of <11.1 mM. Data points represent blood glucose (mM) mean or human C-peptide (pM)±s.e.m.

When the subcutaneous site in diabetic mice was prepared in accordance with our invention, the ensuing stem cell infusion within the void created by the catheter withdrawal, differentiated over time and reversed diabetes in 66.7% (n=4 of 6) of the recipients transplanted, within 107±15.4 days post-transplant (FIG. 11(a)). Recipients that became euglycemic post-transplant demonstrated normal non-fasting blood glucose profiles until the IPS transplant was removed; returning the animals to a pre-transplant diabetic state (FIG. 11(b)). Recipient serum human C-peptide levels were measured 12, 18 and 20 weeks post-transplant following an overnight fasting period and 60 min subsequent to a glucose challenge. Stimulated serum C-peptide progressively increased from 12-20 weeks post-transplant indicting that the human IPS were surviving and differentiating within the DL site. Serum C-peptide levels were abolished post-removal of the IPS transplant (FIG. 11(c)).

Example 12

Figure 12:
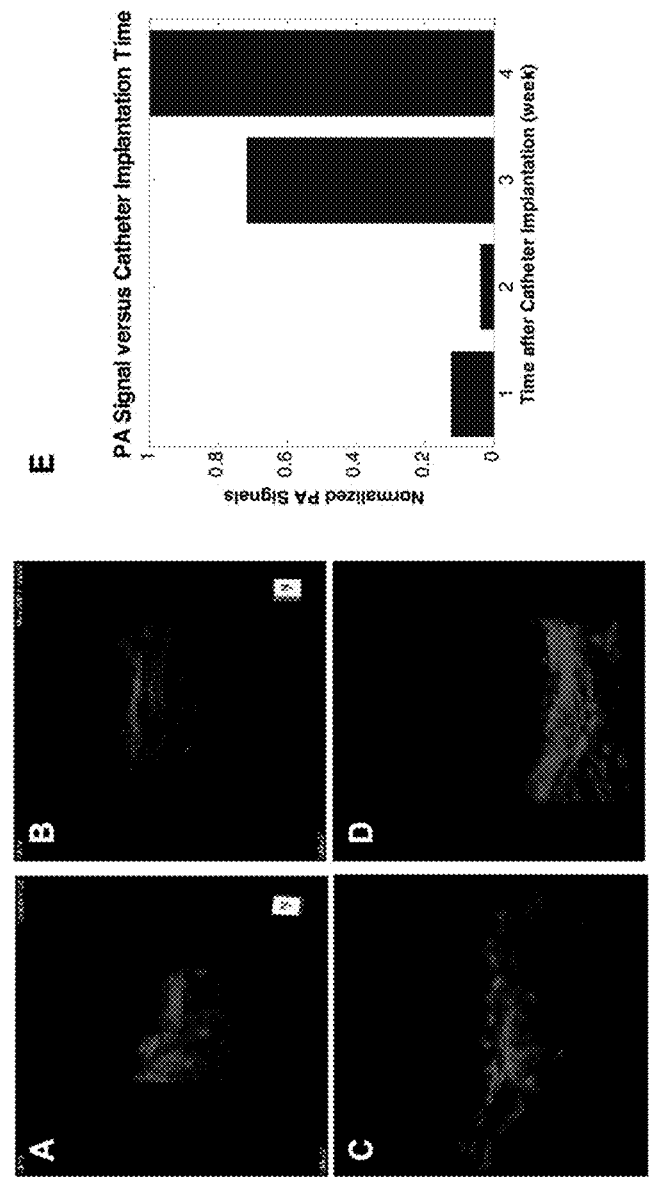
FIG. 12. Photoacoustic (PA) and micro-ultrasound images of peri-catheter angiogenesis in mice at 1 week (A), 2 weeks (B), 3 weeks (C) and 4 weeks (D) post-implantation. Quantitative analysis of PA signals after 1-4 week catheter implantation (E).

Using photoacoustic and micro-ultrasound imaging we have tracked the abdominal angiogenesis profile of mice implanted with catheter segments 1, 2, 3 and 4 weeks post-implant using the clinically translational FujiFilm VisualSonics Vevo-LAZR system with a linear transducer mounted perpendicular to a linear motor to realize 3D imaging. Images before removing implant were taken as well to indicate the implant position once the implant was removed. Multi-wavelength excitation is used for further oxygenation studies. Quantitative analysis on vessel densities shows the gradually growth of vasculature in the implant position, indicating vessel growth successfully induced by the implanted catheter (FIG. 12). This work demonstrates the ability to track angiogenesis around catheter sites prior to islet transplantation to optimize the timeframe for cellular infusion.

Example 13

Figure 13:
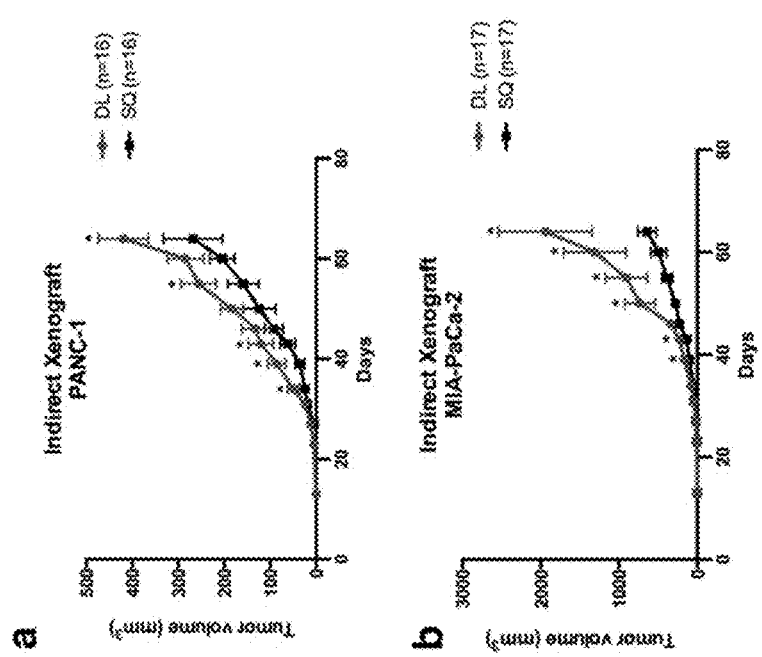
FIG. 13. Average tumor volume of pancreatic tumor cell lines PANC-1 (A) and MIA-PaCa-2 (B) post-transplant into NODscid gamma mice. Mice were transplanted using either the traditional subcutaneous inoculation technique (SQ) or the pre-vascularized deviceless approach (DL).

The subcutaneous transplant technique as a potential site to improve pancreatic cancer cell line implantation. NOD-scid gamma mice were implanted with medically approved angiocatheters on the right flank for 6 weeks. Catheters were then removed and pancreatic cell lines were injected in the potential space created by the catheter on the right side with a subcutaneous inoculation (SubQ) on the left side. Mice were divided into 2 groups; MIA-PaCa-2 (aggressive) and PANC-1 (moderate) cell lines respectively. Initially, tumour volume showed similar growth pattern. However, at 50 days post implantation, the average tumour volume for both pancreatic tumour cell lines, MIA-PaCa-2 and PANC-1 were significantly larger using our transplant technique verses traditional subcutaneous cellular injection (p<0.05, unpaired t-test) (FIG. 13). This observation remained throughout the study period. This work demonstrates that our transplant technique is superior to the conventional subcutaneous inoculation method and could potentially improve engraftment and survival for certain tumors that cannot be implanted by conventional methods; thus providing a model to test patient specific tumor sensitivity to chemotherapeutic agent directing clinical intervention.

DEFINITIONS AND INTERPRETATION

As will be apparent to those skilled in the art, various modifications, adaptations and variations of the foregoing specific disclosure can be made without departing from the scope of the invention claimed herein. The various features and elements of the invention described herein may be combined in a manner different than the specific examples described or claimed herein without departing from the scope of the invention. In other words, any element or feature may be combined with any other element or feature in different embodiments, unless there is an obvious or inherent incompatibility between the two, or it is specifically excluded.

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The term "and/or" means any one of the items, any combination of the items, or all of the items with which this term is associated. The phrase "one or more" is readily understood by one of skilled in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by the skilled artisan, all numbers, including those expressing quantities of reagents or ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

REFERENCES

The following references are incorporated herein by reference in their entirety, where permitted, and may be indicative of the level of skill of those skilled in the art.

1. Shapiro, A. M. et al. Islet transplantation in seven patients with type 1 diabetes mellitus using a glucocorticoid-free immunosuppressive regimen. *N Engl J Med* 343, 230-238 (2000).
2. Ryan, E. A. et al. Five-year follow-up after clinical islet transplantation. *Diabetes* 54, 2060-2069 (2005).
3. Ricordi, C. & Strom, T. B. Clinical islet transplantation: advances and immunological challenges. *Nature reviews. Immunology* 4, 259-268 (2004).
4. Shapiro, A. M. in Islet transplantation and beta cell replacement therapy. (ed. A. M. Shapiro, Shaw J. A.) (Informa Healthcare, New York, London; 2007).
5. Harlan, D. M., Kenyon, N. S., Korsgren, O. & Roep, B. O. Current advances and travails in islet transplantation. *Diabetes* 58, 2175-2184 (2009).
6. Plesner, A. & Verchere, C. B. Advances and challenges in islet transplantation: islet procurement rates and lessons learned from suboptimal islet transplantation. *J Transplant* 2011, 979527 (2011).
7. Olsson, R., Maxhuni, A. & Carlsson, P. O. Revascularization of transplanted pancreatic islets following culture with stimulators of angiogenesis. *Transplantation* 82, 340-347 (2006).
8. Brissova, M. & Powers, A. C. Revascularization of transplanted islets: can it be improved? *Diabetes* 57, 2269-2271 (2008).
9. Pepper, A. R., Gala-Lopez, B., Ziff, O. & Shapiro, A. M. Revascularization of transplanted pancreatic islets and role of the transplantation site. *Clin Dev Immunol* 2013, 352315 (2013).

10. Merani, S., Toso, C., Emamaullee, J. & Shapiro, A. M. Optimal implantation site for pancreatic islet transplantation. *The British journal of surgery* 95, 1449-1461 (2008).
11. Veriter, S., Gianello, P. & Dufrane, D. Bioengineered sites for islet cell transplantation. *Curr Diab Rep* 13, 745-755 (2013).
12. Nishimura, R. et al. Assessment for revascularization of transplanted pancreatic islets at subcutaneous site in mice with a highly sensitive imaging system. *Transplant Proc* 43, 3239-3240 (2011).
13. Saito, T. et al. Reversal of diabetes by the creation of neo-islet tissues into a subcutaneous site using islet cell sheets. *Transplantation* 92, 1231-1236 (2011).
14. Sakata, N. et al. Strategy for clinical setting in intramuscular and subcutaneous islet transplantation. *Diabetes Metab Res Rev* (2013).
15. Simeonovic, C. J., Dhall, D. P., Wilson, J. D. & Lafferty, K. J. A comparative study of transplant sites for endocrine tissue transplantation in the pig. *Aust J Exp Biol Med Sci* 64 (Pt 1), 37-41 (1986).
16. Rajab, A. Islet transplantation: alternative sites. *Curr Diab Rep* 10, 332-337 (2010).
17. Anderson, J. M., Rodriguez, A. & Chang, D. T. Foreign body reaction to biomaterials. *Semin Immunol* 20, 86-100 (2008).
18. Grainger, D. W. All charged up about implanted biomaterials. *Nat Biotechnol* 31, 507-509 (2013).
19. Kin, T, et al. Risk factors for islet loss during culture prior to transplantation. *Transpl Int* 21, 1029-1035 (2008).
20. Ricordi, C., Lacy, P. E. & Scharp, D. W. Automated islet isolation from human pancreas. *Diabetes* 38 Suppl 1, 140-142 (1989).
21. Anderson, J. M. Biological response to materials. *Annual Review of Materials Research* 31, 81-110 (2001).
22. Kenneth Ward, W. A review of the foreign-body response to subcutaneously-implanted devices: the role of macrophages and cytokines in biofouling and fibrosis. *J Diabetes Sci Technol* 2, 768-777 (2008).
23. Fujiwara, N. & Kobayashi, K. Macrophages in inflammation. *Curr Drug Targets Inflamm Allergy* 4, 281-286 (2005).
24. Nyqvist, D. et al. Donor islet endothelial cells in pancreatic islet revascularization. *Diabetes* 60, 2571-2577 (2011).
25. Brauker, J. H. et al. Neovascularization of synthetic membranes directed by membrane microarchitecture. *J Biomed Mater Res* 29, 1517-1524 (1995).
26. Sharkawy, A. A., Klitzman, B., Truskey, G. A. & Reichert, W. M. Engineering the tissue which encapsulates subcutaneous implants. III. Effective tissue response times. *J Biomed Mater Res* 40, 598-605 (1998).
27. Wilson, C. J., Clegg, R. E., Leavesley, D. I. & Pearcy, M. J. Mediation of biomaterial-cell interactions by adsorbed proteins: a review. *Tissue Eng* 11, 1-18 (2005).
28. Hu, W. J., Eaton, J. W., Ugarova, T. P. & Tang, L. Molecular basis of biomaterial-mediated foreign body reactions. *Blood* 98, 1231-1238 (2001).
29. Broughton, G., 2nd, Janis, J. E. & Attinger, C. E. The basic science of wound healing. *Plast Reconstr Surg* 117, 12S-34S (2006).
30. Kvist, P. H, et al. Biocompatibility of an enzyme-based, electrochemical glucose sensor for short-term implantation in the subcutis. *Diabetes Technol Ther* 8, 546-559 (2006).
31. Sharkawy, A. A., Klitzman, B., Truskey, G. A. & Reichert, W. M. Engineering the tissue which encapsulates subcutaneous implants. I. Diffusion properties. *J Biomed Mater Res* 37, 401-412 (1997).
32. Sharkawy, A. A., Klitzman, B., Truskey, G. A. & Reichert, W. M. Engineering the tissue which encapsulates subcutaneous implants. II. Plasma-tissue exchange properties. *J Biomed Mater Res* 40, 586-597 (1998).
33. Zhang, L. et al. Zwitterionic hydrogels implanted in mice resist the foreign-body reaction. *Nat Biotechnol* 31, 553-556 (2013).
34. Zhang, H. F., Maslov, K., Stoica, G. & Wang, L. V. Functional photoacoustic microscopy for high-resolution and noninvasive in vivo imaging. *Nat Biotechnol* 24, 848-851 (2006).
35. Deisseroth, K. Optogenetics. *Nat Methods* 8, 26-29 (2011).
36. Olsson, R., Olerud, J., Pettersson, U. & Carlsson, P. O. Increased numbers of low-oxygenated pancreatic islets after intraportal islet transplantation. *Diabetes* 60, 2350-2353 (2011).
37. Pileggi, A., Ricordi, C., Alessiani, M. & Inverardi, L. Factors influencing Islet of Langerhans graft function and monitoring. *Clinica chimica acta; international journal of clinical chemistry* 310, 3-16 (2001).
38. Juang, J. H., Peng, S. J., Kuo, C. H. & Tang, S. C. 3D islet graft histology: panoramic imaging of neural plasticity in sympathetic reinnervation of transplanted islets under the kidney capsule. *American journal of physiology. Endocrinology and metabolism* (2014).
39. Stendahl, J. C., Kaufman, D. B. & Stupp, S. I. Extracellular matrix in pancreatic islets: relevance to scaffold design and transplantation. *Cell Transplant* 18, 1-12 (2009).

What is claimed is:

1. A method of cellular transplantation in a mammal, comprising the steps of:
    (a) inserting a foreign body comprising a hydrophilic biomaterial into an internal tissue, without an exogenous biological factor, wherein the biomaterial has a water contact angle of less than 90° and a critical surface tension of greater than 20 dynes/cm;
    (b) removing the entire foreign body after tissue surrounding the foreign body has undergone a foreign body response, leaving a neovascularized lumen suitable to receive transplanted cells; and
    (c) transplanting cells into the neovascularized lumen.

2. The method of claim 1 wherein the entire foreign body is removed before fibrous encapsulation of the transplant site occurs.

3. The method of claim 1 wherein the internal tissue space comprises a subcutaneous layer, a peritoneal layer, intramuscular layer, sub-mucosal layer, intra-bone marrow, intra-organ layer or an organ.

4. The method of claim 1 wherein the hydrophilic biomaterial has a textured or porous surface, or both a textured and porous surface.

5. The method of claim 1 wherein the hydrophilic biomaterial comprises a nylon catheter segment.

6. The method of claim 1 wherein the biomaterial is a catheter or is shaped like a catheter and has an outer diameter less than 2.2 mm.

7. The method of claim 6 wherein the biomaterial has an outer diameter of less than 1.7 mm.

8. The method of claim 1 wherein the biomaterial comprises a zwitterionic polymer.

9. A method of cellular transplantation in a mammal, comprising the steps of:

(a) inserting a hydrophilic foreign body biomaterial into an internal tissue;
(b) removing the entire foreign body after tissue surrounding the foreign body has undergone a foreign body response, leaving a neovascularized lumen suitable to receive transplanted cells; and
(c) transplanting cells into the neovascularized lumen.

10. The method of claim 9 wherein the biomaterial has a water contact angle of less than 90° and a critical surface tension of greater than 20 dynes/cm.

11. The method of claim 9 wherein the hydrophilic biomaterial has a textured or porous surface, or both a textured and porous surface.

12. The method of claim 9 wherein the biomaterial comprises nylon.

13. The method of claim 9 wherein the biomaterial comprises a zwitterionic polymer.

* * * * *